United States Patent
Yamamoto

(10) Patent No.: US 12,305,208 B2
(45) Date of Patent: May 20, 2025

(54) METHOD FOR PRODUCING SEDOHEPTULOSE

(71) Applicant: NAGASE & CO., LTD., Osaka (JP)

(72) Inventor: Shogo Yamamoto, Kobe (JP)

(73) Assignee: NAGASE & CO., LTD., Osaka (JP)

( * ) Notice: Subject to any disclaimer, the term of this patent is extended or adjusted under 35 U.S.C. 154(b) by 0 days.

(21) Appl. No.: 18/454,874

(22) Filed: Aug. 24, 2023

(65) Prior Publication Data

US 2023/0407354 A1 Dec. 21, 2023

Related U.S. Application Data

(62) Division of application No. 17/049,789, filed as application No. PCT/JP2019/017832 on Apr. 26, 2019, now Pat. No. 11,781,165.

(30) Foreign Application Priority Data

Apr. 27, 2018 (JP) ................................. 2018-087503

(51) Int. Cl.
*C12P 19/02* (2006.01)
*C12N 9/00* (2006.01)
*C12N 9/10* (2006.01)
*C12N 9/90* (2006.01)

(52) U.S. Cl.
CPC ............ *C12P 19/02* (2013.01); *C12N 9/1022* (2013.01); *C12N 9/90* (2013.01); *C12N 9/93* (2013.01); *C12Y 202/01002* (2013.01); *C12Y 504/99016* (2013.01); *C12Y 604/01003* (2013.01)

(58) Field of Classification Search
CPC ......... C12P 19/02; C12N 9/1022; C12N 9/90; C12N 9/93; C12Y 504/99016; C12Y 604/01003
See application file for complete search history.

(56) References Cited

FOREIGN PATENT DOCUMENTS

| | | |
|---|---|---|
| EP | 1 174 508 A2 | 1/2002 |
| JP | 39-14500 B | 7/1964 |
| JP | 41-4400 B | 3/1966 |
| JP | 41-5915 B | 3/1966 |
| JP | 41-21760 B | 12/1966 |
| JP | 62-126990 A | 6/1987 |
| JP | 2003-520583 A | 7/2003 |
| JP | 2017-506078 A | 3/2017 |
| SK | 284 318 B6 | 1/2005 |

OTHER PUBLICATIONS

International Search Report issued on Jul. 16, 2019 in PCT/JP2019/017832 filed Apr. 26, 2019, 1 page.
Okuda et al., "Accumulation of Sedoheptulose by Streptomycetes", The Journal of Biochemistry, 1963, vol. 54, No. 1, pp. 107-108.

(Continued)

*Primary Examiner* — Iqbal H Chowdhury
(74) *Attorney, Agent, or Firm* — Oblon, McClelland, Maier & Neustadt, L.L.P.

(57) ABSTRACT

Sedoheptulose, which is a saccharide falling within the categories of ketoses and heptuloses, is one of a small number of heptuloses occurring in nature. Provided are a method for producing sedoheptulose using a bacterium owing to the deletion or attenuation of a specific enzymatic function, a method for improving the productivity of sedoheptulose by the bacterium, and the bacterium.

2 Claims, 2 Drawing Sheets

Specification includes a Sequence Listing.

(56) References Cited

OTHER PUBLICATIONS

Dalmas et al., "An Efficient Synthesis of Sedoheptulose Catalyzed by Spinach Transketolase", 1993, Tetrahedron: Asymmetry, vol. 4, No. 6, pp. 1169-1172.
Villafranca et al., "Heptulose Synthesis from Nonphosphorylated Aldoses and Ketoses by Spinach Transketolase", The Journal of Biological Chemistry, 1971, vol. 246, No. 10, pp. 3126-3131 (7 total pages).
Arabolaza et al., "Crystal Structures and Mutational Analyses of Acyl-CoA Carboxylase β Subunit of *Streptomyces coelicolor*", Biochemistry, 2010, vol. 49, No. 34, pp. 1-21.
Mitova et al., "Subinhibitory Concentrations of Antibiotics Induce Phenazine Production in a Marine *Streptomyces* sp.",. Journal of Natural Products, 2008, vol. 71, No. 5, pp. 824-827.
Schaaff et al., "Molecular analysis of the structural gene for yeast transaldolase", European Journal of Biochemistry, 1990, vol. 188, pp. 597-603, ISSN: 0014-2956.
Extended European Search Report issued Jan. 4, 2022 in European Patent Application No. 19791770.1, 8 pages.
Yota Tsuge, et al . . . "Metabolic engineering of *Corynebacterium glutamicum* for production of sunscreen shinorine," Bioscience, Biotechnology, and Biochemistry, vol. 82, No. 7, XP055751051, 2018, 9 pages.
International Preliminary Report on Patentability and Written Opinion issued Nov. 5, 2020 in PCT/JP2019/017832 (with English Translation), 11 pages.
Schaaf et al., "Molecular Analysis of the Structural Gene for Yeast Transaldolase", *Eur. J. Biochem.* (1990), 188: 597-603.
Kiyoko T. Miyamoto et al., Discovery of Gene Cluster for Mycosporine-Like Amino Acid Biosynthesis from Actinomycetales Microorganisms and Production of a Novel Mycosporine-Like Amino Acid by Heterologous Expression, Journals ASM. Org., Applied and Environmental Microbiology, Aug. 2014, vol. 80, No. 16, pp. 5028-5036 (Appendix A).
Shiori Doi, et al., Modifications to central carbon metabolism in an engineered Streptomyces host to enhance secondary metabolite production, Journal of Bioscience and Bioengineering, vol. 130, No. 6, 563-570, 2020 (Appendix B).
Office Action issued on Aug. 9, 2024, in the corresponding European patent application No. 19791770.1, 7 pages.
Kenji Nakahigashi et.al.: "Systematic phenome analysis of *Escherichia coli* multiple-knockout mutants reveals hidden reaction in central carbon metabolism," Molecular Systems Biology, vol. 5, No. 1, Jan. 1, 2009, pp. 1-14.
Japanese Office Action issued Aug. 13, 2024 in Japanese Patent Application No. 2023-125390 (with unedited, machine-generated English translation, 7 pages.
Borodina, et al., Metabolism and Bioenergetics: Antibiotic Overproduction in Streptomyces coelicolor A3(2) Mediated by Phosphofructokinase Deletion, The Journal of Biological Chemistry, vol. 283, No. 37, pp. 25186-25199, Sep. 12, 2008.
Siedler, et al., Reductive whole-cell blotransformation with Corynebacterium glutamicum: improvement of NADPH generation from flucose by a cyclized pentose phosphate pathway using ptkA and gapA deletion mutants. Appl Microbiol Blootyechnol (2013) 97:pp. 143-162, DOI 10.1007/800253-012-4314-7.

ial stage of PCT/JP2019/017832 filed Apr. 26, 2019

SEQUENCE LISTING

```
Sequence total quantity: 32
SEQ ID NO: 1              moltype = AA   length = 372
FEATURE                   Location/Qualifiers
source                    1..372
                          mol_type = protein
                          organism = Streptomyces lividans
SEQUENCE: 1
MTDALKRLSD EGVAIWLDDL SRKRITSGNL AELIDQQHVV GVTTNPSIFQ KAISQGDGYD   60
QQLADLAVRG VTVEEAIRMI TTADVRDAAD ILRPVYDNTG GKDGRVSIEV DPRLAHNTHA  120
TVAEAKQLAW LVDRPNTFIK IPATEAGLPA IAETIGLGIS VNVTLIFSLE RYRKVMDAFL  180
TGLEKAKERG LDLSQIHSVA SFFVSRVDTE IDKRIDALGT DEAKAQRGKA AVANARLAYQ  240
AYEEVFGTDR WAALEKAGAN KQRPLWASTG VKDKAYSDTM YVTDLVAPNT VNTMPEATLL  300
ATEDHGEITG DAVAGSYERA RADLDAIEKL GISYDEVVQL LEKEGVDKFE DAWNDLLKST  360
EAELKRLAPS KG                                                     372

SEQ ID NO: 2              moltype = AA   length = 381
FEATURE                   Location/Qualifiers
source                    1..381
                          mol_type = protein
                          organism = Streptomyces lividans
SEQUENCE: 2
MITVTEATAT AGALQRLADQ GVSVWLDDLS RRRIESGNLA ELIRTKNVVG VTTNPSIFQA   60
AIGSGEGYEE QLADLATRGV TVDEAVRMMT TADVRAAADV LRGVYDASGG RDGRVSIEVD  120
PRLAHDTAAT VAEARQLSWL VDRPNVMIKI PATKAGLPAI TEVIGAGISV NVTLIFSLER  180
YREVMDAYLA GLEKAQAAGI DLAGIHSVAS FFVSRVDSEI DKRLSLLGTE EALGLRGRAA  240
LANARLAYEA YENVFAGDRF TALAGARANP QRPLWASTGV KDPAFRDTLY VEELVAPGTV  300
NTMPEATLDA AADHGDVRGD TVTGGYAQAR ADLAAVERLG VSYDEVVEQL EQEGVAKFEA  360
AWQELLAAVT KSLDSKGVDG E                                           381

SEQ ID NO: 3              moltype = AA   length = 372
FEATURE                   Location/Qualifiers
source                    1..372
                          mol_type = protein
                          organism = Streptomyces avermitilis
SEQUENCE: 3
MTDALKRLSK EGVAIWLDDL SRKRITSGNL AELIDQQHVV GVTTNPSIFQ KAISQGDGYD   60
QQVSDLAARR VTVEEAIRMI TTADVRDAAD ILRPVFDATD GQDGRVSIEV DPRLAHNTKA  120
TVAEAKQLAW LVDRPNTLIK IPATKAGIPA ITEVIGLGIS VNVTLIFSLE RYRMVMDAYL  180
AGLEKAKERG LDLSKIHSVA SFFVSRVDTE IDKRIDALGT PEAKAARGKA GLANARLAYE  240
AYEAVFSTDR WLALDKAQAN KQRPLWASTG VKDPAYKDTM YVEELVAPNT VNTMPEATLE  300
ATADHGEIRG NTIAGTYEQA RADLDAVEKL GIAYDDVVQL LEEEGVDKFE ASWNDLLKST  360
EAELQRLAPS EG                                                     372

SEQ ID NO: 4              moltype = AA   length = 378
FEATURE                   Location/Qualifiers
source                    1..378
                          mol_type = protein
                          organism = Streptomyces avermitilis
SEQUENCE: 4
MITVSNTVEN LERLSDEGVS IWLDDLSRKR ITSGNLAELI AHKHVVGVTT NPSIFQAAIG   60
SGEGYEEQLA DLAVRGVTVD EAVRMMTTAD VRAAADILRP VYDATGGRDG RVSIEVDPRL  120
AHDTEATIAE AKQLAWLVDR PNVMIKIPAT KAGLPAITEV IGLGISVNVT LIFSLERYRE  180
VMDAYLAGLE RAQAAGIDLA GIHSVASFFV SRVDSEIDKR LAKAGTDDAQ ALKGKAALAN  240
ARLAYEAYEE VFAGERWTAL APAGAHKQRP LWASTGVKDP AYKDTLYVDE LVAPGTVNTM  300
PEGTLNATAD HGDIHGDTVT GGYAQARADL AAVERLGISY DEVVKQLEDE AVAKFEVAWG  360
DLLEAVATSL RGKGADGE                                               378

SEQ ID NO: 5              moltype = AA   length = 530
FEATURE                   Location/Qualifiers
source                    1..530
                          mol_type = protein
                          organism = Streptomyces lividans
SEQUENCE: 5
MSEPEEQQPD IHTTAGKLAD LRRRIEEATH AGSARAVEKQ HAKGKLTARE RIDLLLDEGS   60
FVELDEFARH RSTNFGLDAN RPYGDGVVTG YGTVDGRPVA VFSQDFTVFG GALGEVYGQK  120
IVKVMDFALK TGCPVVGIND SGGARIQEGA ASLGAYGEIF RRNTHASGVI PQISLVVGPC  180
AGGAVYSPAI TDFTVMVDQT SHMFITGPDV IKTVTGEDVG FEELGGARTH NTASGVAHHM  240
AGDEKDAVEY VKQLLSYLPS NNLSEPPAFP EEADLAVTDE DAELDAIVPD SANQPYDMHS  300
VIEHVLDDGE FFETQPLFAP NILTGFGRVE GRPVGIVANQ PMQFAGCLDI TASEKAARFV  360
RTCDAFNVPV LTFVDVPGFL PGVDQEHDGI IRRGAKLIFA YAEATVPLIT VITRKAFGGA  420
YDVMGSKHLG ADLNLAWPTA QIAVMGAQGA VNILHRRTIA DAGDDAEATR ARLIQEYEDA  480
LLNPYTAAER GYVDAVIMPS DTRRHIVRGL RQLRTKRESL PPKKHGNIPL            530

SEQ ID NO: 6              moltype = AA   length = 532
FEATURE                   Location/Qualifiers
source                    1..532
                          mol_type = protein
                          organism = Streptomyces avermitilis
```

```
SEQUENCE: 6
MSEPEELHHP DIHTTAGKLA DLQRRIQEAT HAGSERAVEK QHAKGKLTAR ERIALLLDED    60
SFVELDEFAQ HRSTDFGMEN NRPYGDGVVT GYGTVDGRPV AVFSQDFTVF GGALGEVFGQ   120
KIMKAMDFAL KTGCPVIGIN DSGGARIQEG VSALGMYGEI FRRNTHASGV IPQISLVVGP   180
CAGGAVYSPA ITDFTVMVDQ TSHMFITGPD VIKTVTGEDV GFEELGGART HNAVSGVAHH   240
MAGEEEKDAIE YVKQLLSYLP SNNLSEPPAF PEEADLALTD EDRELDTLVP DSANQPYDMH   300
TVIEHILDDA EFLETQPLFA PNILTGFGRV EGHPVGIVAN QPMQFAGCLD IDASEKAARF   360
VRTCDAFNVP VITFVDVPGF LPGVGQEHDG IIRRGAKLIY AYAEATVPLI TVITRKAFGG   420
AYDVMGSKHL GADLNLAWPT AQIAVMGAQG AVNILHRRTI AATPEEEREE VRRRLIQEYE   480
DTLLNPYTAA ERGYIDGVIM PSDTRAHVVR GLRQLRTKRE SLPPKKHGNI PL          532

SEQ ID NO: 7               moltype = AA   length = 572
FEATURE                    Location/Qualifiers
source                     1..572
                           mol_type = protein
                           organism = Streptomyces lividans
SEQUENCE: 7
MTVNEPVPDT FEDTPAGDRH PDWFKRAVFY EVLVRSFQDS NGDGIGDLKG LTAKLDYLQW    60
LGVDCLWLPP FFKSPLRDGG YDVSDYTAVL PEFGDLADFV EFVDAAHQRG MRVIIDFVMN   120
HTSDQHPWFQ ESRKNPDGPY GDYYVWADDD TRYADARIIF VDTEASNWTY DPVRGQYYWH   180
RFFSHQPDLN YENPAVQEEM LAALKFWLDL GVDGYRLDAV PYLYAEEGTN CENLPASHAF   240
LKRVRREIDA QYPDTVLLAE ANQWPEDVVD YFGDYSTGGD ECHMAFHFPV MPRIFMAVRR   300
ESRYPVSEIL AKTPAIPSGC QWGIFLRNHD ELTLEMVTDE ERDYMYAEYA KDPRMRANIG   360
IRRRLATLLD NDRDQIELFT ALLLALPGSP ILYYGDEIGM GDNIWLGRD AVRTPMQWTP    420
DRNAGFSTCD PGRLYLPAIM DPVYGYQVTN VEASMASPSS LLHWTRRMIE IRKQNPAFGL   480
GTYTELPSSN PAVLAFLREY EDDLVLCVNN FARFAQPTEL DLREFAGRHP VELFGGVRFP   540
AIGELPYLLT LGGHGFYWFR LTRVASRIGR RA                                 572

SEQ ID NO: 8               moltype = AA   length = 583
FEATURE                    Location/Qualifiers
source                     1..583
                           mol_type = protein
                           organism = Streptomyces avermitilis
SEQUENCE: 8
MIVNEPVPDT FEDTPAKDRD PEWFKRAVFY EVLVRSFQDS NGDGVGDLKG LTAKLDYLQW    60
LGVDCLWLPP FFKSPLRDGG YDVSDYTAVL PEFGDLADFV EFVDAAHQRG MRVIIDFVMN   120
HTSDLHPWFQ ESRSNPDGPY GDYYVWADDD KQYQDARIIF VDTEASNWTY DPVRKQYYWH   180
RFFSHQPDLN YESAAVQEEI LAALRFWLDL GIDGFRLDAV PYLYNEEGTN CENLPATHEF   240
LKRVRKEIDT HYPDTVLLAE ANQWPEDVVD YFGDFPSGGD ECHMAFHFPV MPRIFMAVRR   300
ESRYPVSEIL AKTPAIPSSC QWGIFLRNHD ELTLEMVTDE ERDYMWAEYA KDPRMRANIG   360
IRRRLAPLLD NDRNQIELFT ALLLSLPGSP ILYYGDEIGM GDNIWLGRD AVRTPMQWTP    420
DRNAGFSSCD PGRLYLPTIM DPVYGYQVTN VEASMSSPSS LLHWTRRMIE IRKQNPAFGL   480
GSYTELQSSN PAVLAFLREA PSTGGNGDDL VLCVHNFSRF AQPTELDLRA FSGRHPVELI   540
GGVRFPAIGE LPYLLTLAGH GFYWFRLRKD VTQVTKVSLF VSS                     583

SEQ ID NO: 9               moltype = AA   length = 566
FEATURE                    Location/Qualifiers
source                     1..566
                           mol_type = protein
                           organism = Streptomyces lividans
SEQUENCE: 9
MTVNEPVPDT FEDTPAGDRH PDWFKRAVFY EVLVRSFQDS NGDGIGDLKG LTAKLDYLQW    60
LGVDCLWLPP FFKSPLRDGG YDVSDYTAVL PEFGDLADFV EFVDAAHQRG MRVIIDFVMN   120
HTSDQHPWFQ ESRRNPDGPY GDYYVWADDD KQFQDARIIF VDTEASNWTY DPVRKQYYWH   180
RFFSHQPDLN YENPVVQEEM ISALKFWLDL GIDGFRLDAV PYLYQEEGTN CENLPRTHDF   240
LKRVRKEIDA QYPDTVVLAE ANQWPEDVVD YFGDYAAGGD ECHMAFHFPV MPRIFMAVRR   300
ESRYPVSEIL AKTPAIPSGC QWGIFLRNHD ELTLEMVTDE ERDYMYAEYA KDPRMRANIG   360
IRRRLAPLLD NDRNQIELFT ALLLSLPGSP ILYYGDEIGM GDNIWLGRD AVRTPMQWTP    420
DRNAGFSSSD PGRLFLPTIM DPVHGYQVTN VEASMSSPSS LLHWTRRMIE IRKQNVAFGL   480
GTYTELPSSN PAVLAFLREH EDDLVLCVHN FSRFAQPTEL DLSAFDGRHP VELFGGVRFP   540
AVGDLPYLLT LGGHGFYWFR LRKDAA                                        566

SEQ ID NO: 10              moltype = AA   length = 572
FEATURE                    Location/Qualifiers
source                     1..572
                           mol_type = protein
                           organism = Streptomyces avermitilis
SEQUENCE: 10
MIVNEPVPDT FEDTPAKDRD PEWFKRAVFY EVLVRSFQDS NGDGVGDLKG LTAKLDYLQW    60
LGVDCLWLPP FFKSPLRDGG YDVSDYTAVL PEFGDLADFV EFVDAAHQRG MRVIIDFVMN   120
HTSDLHPWFQ ESRSNPDGPY GDYYVWADDD KQYQDARIIF VDTEASNWTF DPVRKQYYWH   180
RFFSHQPDLN YENPAVQEEI VSALRFWLDL GIDGFRLDAV PYLYQQEGTN CENLPATHEF   240
LKRVRKEIDT HYPDTVLLAE ANQWPEDVVD YFGDFPSGGD ECHMAFHFPV MPRIFMAVRR   300
ESRYPVSEIL AKTPAIPSSC QWGIFLRNHD ELTLEMVTDE ERDYMWAEYA KDPRMRANIG   360
IRRRLAPLLD NDRNQIELFT ALLLSLPGSP ILYYGDEIGM GDNIWLGRD AVRTPMQWTP    420
DRNAGFSSCD PGRLYLPTIM DPVYGYQVTN VEASMSSPSS LLHWTRRMIE IRKQNPAFGL   480
GSYTELQSSN PAVLAFLREA PSTGGNGDDL VLCVHNFSRF AQPTELDLRA FSGRHPVELI   540
GGVRFPAIGE LPYLLTLAGH GFYWFRLRKD AV                                 572
```

```
SEQ ID NO: 11            moltype = AA   length = 704
FEATURE                  Location/Qualifiers
source                   1..704
                         mol_type = protein
                         organism = Streptomyces lividans
SEQUENCE: 11
VFMQVWPGEA YPLGATYDGA GTNFAVFTEA ADRVELCLLH DDGSETAVEL RESDAFVRHA    60
YVPGVMPGQR YGYRVHGPYA PERGLRCNSA KLLLDPYARA ISGEVQWGEE VYGYHFGAPE   120
RRNDLDSAPH TMTSVVVNPY FDWGDDRRPR TEYHHTVIYE AHVKGLTMRH PGLPEELRGT   180
YAALAHPALI EHLTGLGVTA LELMPVHQFV NDHRLVDMGL NNYWGYNTVG FFAPHNAYAS   240
WGDRGQQVLE FKSAVKALHE AGIEVILDVV YNHTAEGNHL GPTLSFKGLD NPSYYRLADD   300
PRYYMDTTGT GNSLLMRSPH VLQMIMDSLR YWVTEMHVDG FRFDLAATLA RQFHEVDRLS   360
SFFDLVQQDP VVSQVKLIAE PWDVGEGGYQ VGNFPPLWTE WNGKYRDTVR DLWRGEPRTL   420
AEFASRLTGS SDLYQDDGRR PLASINFVTC HDGFTLHDMV AYNDKHNHAN GEDNRDGESH   480
NRSWNCGVEG DTDDPAVLEL RARQMRNFIA TLLLSQGVPM LSHGDEFART QRGNNNAYCQ   540
DNELAWVAWP EDGHDLLEFT RAMVWLRKDH PVLRRRRFFH GRPVQGTHDE LSDIAWFTPE   600
GAEMAQRDWN SARASALTVF LNGNAISEPG TRGERIADDS FLLMFNAAPR PLDFVVPVDH   660
GRQWEVVVDT ALTAGVPTGT GPKVQAGDRL TLLDRSLTVL QRPV                    704

SEQ ID NO: 12            moltype = AA   length = 702
FEATURE                  Location/Qualifiers
source                   1..702
                         mol_type = protein
                         organism = Streptomyces avermitilis
SEQUENCE: 12
MQVWPGEAYP LGATYDGAGT NFAVFSEAAH RIELCLLHDD GSETAVELRE TDAFVRHAYL    60
PGVMPGQRYG FRVHGPFAPG RGVRCNSAKL LLDPYAKAIS GEIKWGEEVY GYHFGAPDKR   120
NDLDSAPHTM TSVVINPYFD WGNDRRPRTE YHHTVLYEAH VKGLTMRHPA LPEELRGTYA   180
ALAHPAIIEH LTELGVTALE LMPVHQFVND HRLVDMGLNN YWGYNTIGFF APHNAYASWG   240
DRGQQVLEFK SAVKALHEAG IEVILDVVYN HTAEGNHMGP TLSFKGIDNA SYYRLTDDPR   300
YYMDTTGTGN SLLMRSPHVL QLIMDSLRYW VSDMHVDGFR FDLAATLARQ FHEVDRLSSF   360
FDLVQQDPVV SQVKLIAEPW DVGEGGYQVG NFPPLWTEWN GKYRDTVRDM WRGEPRTLAE   420
FASRLTGSSD LYQDDGRRPL ASINFVTCHD GFTLHDLVAY NDKHNQANGE DNRDGESHNR   480
SWNCGAEGDT DDPAVLALRA RQMRNFIATL MLSQGVPMLS HGDEFARTQG GNNNAYCQDG   540
ELSWVAWPED GSELLEFTRA MVWLRRDHPV FRRRRFFHGR PVEGTHDELS DIVWFTPTGE   600
EMIQRDWDSA QARALTVFLN GTAISEPGPR GERISDDSFL LMFNASPKSL EFVVPVDHGR   660
QWQVVVDTAR TDGIPPGTVA KVKAGDRLTL VDRSLTVLQR PA                      702

SEQ ID NO: 13            moltype = DNA   length = 1119
FEATURE                  Location/Qualifiers
source                   1..1119
                         mol_type = other DNA
                         organism = Streptomyces lividans
SEQUENCE: 13
atgacagacg cactcaagcg cctctccgat gaaggcgtgg cgatctggct ggacgacctg    60
tcgcgcaagc ggatcacgtc cggcaacctc gccgagctga tcgaccagca gcacgtcgtg   120
ggcgtcacca ccaacccgtc gatcttccag aaggccatct cgcagggcga cggctacgac   180
cagcagctcg ccgacctcgc cgtccgcgga gtcacggtcg aagaggccat ccgcatgatc   240
accacggcgg acgtccgcga cgccgccgac atcctgcgcc ccgtctacga caacaccggc   300
ggcaaggacg gccgggtctc catcgaggtg acccgcggc tggcgcacaa cacccacgcc   360
acggtgggca aggccaagca gctgcgtgg ctggtggacc ggccgaacac cttcatcaag   420
atcccggcga ccgaggcggg cctgccggcc atcgccgaga ccatcggcct gggcatcagc   480
gtcaacgtca cgctgatctt ctccctggag cgctaccgca aggtcatgga cgccttcctg   540
accggcctga gaaggccaa ggagcgtggc ctggacctct cgcagatcca ctccgtggcg   600
tccttcttcg tgtcccgcgt ggacaccgag atcgacaagc tgatcgacgc gctcggccac   660
gacgaggcca aggcgcagcg cggcaaggcc gccgtcgcca acgcccgcct ggcctaccag   720
gcgtacgagg agtcttcgg caccgaccgc tgggccgccc tggagaaggc cggcgccaac   780
aagcagcgtc cgctgtgggc gtcgaccggt gtgaaggaca aggcgtacag cgacaccatg   840
tacgtcaccg acctggtcgc gccgaacacg gtcaacacca tgccggagc cacgctgctg   900
gccaccgagg accacggcga gatcaccggc gacgccgtcg ccgggtcgta cgagcgggcc   960
cgcgcggacc tcgacgcgat cgagaagctc gggatctcct acgacgaggt ggtccagctc  1020
ctggagaagg aaggcgtcga caagttcgag gacgcctgga cgacctgct gaagtccacg  1080
gaggcggagc tcaagcgcct cgctcccctcg aagggctga                       1119

SEQ ID NO: 14            moltype = DNA   length = 1146
FEATURE                  Location/Qualifiers
source                   1..1146
                         mol_type = other DNA
                         organism = Streptomyces lividans
SEQUENCE: 14
atgatcactg tgaccgaagc aaccgccacc gcgggagcac tgcagcgcct ggccgaccag    60
ggcgtgtccg tctggctcga cgacctgtcg cggcggcgga tcgagtccgg caacctcgcc   120
gagctgatca ggacgaagaa cgtcgtcgga gtcaccacca cccgtcgat cttccaggcc   180
gccatagct ccggcagggg ctacgaggag cagctcgatc acctgcatca cgtcgacgtg   240
accgtcgacg aggcggtccg catgatgacc accgccgatg tccgcgccgc cgccgacgtg   300
ctgcgcgggg tgtacgacgc ctccggcggg gcgacggcc gcgtctccat cgaggtcgac   360
ccgcgcctgg cccacgacac ggcggcgacg gtcgccgagg cccgccagct gtcctggctg   420
gtcgaccgtc ccaacgtgat gatcaagatc ccggcgacga aggccggtct cccggccatc   480
accgaggtca tcggcgccgg catcagtgtg aacgtcacgc tgatcttctc cctggagcgc   540
```

```
taccgcgagg tcatggacgc ctacctcgcc ggcctggaga aggcgcaggc ggccgggatc    600
gacctggccg gcatccactc ggtcgcgtcc ttcttcgtct cccgcgtcga cagcgagatc    660
gacaagcgcc tgtccctgct gggcaccgaa gaggcgctcg gcctgcgcgg ccgggcggca    720
ctggccaacg cacgactggc ctacgaggcg tacgagaacg tcttcgcggg cgaccgcttc    780
accgccctcg cggggcccg cgcgaacccc cagcgcccc tgtgggcgtc caccggtgtg       840
aaggacccgg cattccggga caccctgtac gtggaggagc tggtcgcccc cggcaccgtg    900
aacacgatgc cggaggccac cctgacgcc gccgccgatc acggcgacgt acggggcgac     960
acggtcaccg gcgggtacgc ccaggcccgc gccgatctcg cggccgtgga gcggctcggc   1020
gtgtcgtacg acgaggtggt ggagcagttg gagcaggagg gcgtggcgaa gttcgaggcg   1080
gcctggcagg agctgctcgc cgccgtgacg aagtccctcg acagcaaggg agttgacggg   1140
gaatga                                                              1146

SEQ ID NO: 15           moltype = DNA  length = 1119
FEATURE                 Location/Qualifiers
source                  1..1119
                        mol_type = other DNA
                        organism = Streptomyces avermitilis
SEQUENCE: 15
atgacagacg cactcaagcg cctctccaag gaaggcgtcg cgatctggct ggacgacctg     60
tcgcgcaagc ggatcacgtc cggcaacctc gccgaactga tcgaccagca gcacgtcgtg   120
ggcgtcacca ccaacccgtc gatcttccag aaggccatct ctcagggcga cggttacgac   180
cagcaggtct ccgacctcgc cgcccgccgg gtcaccgtcg aagaagccat cgcatgatc     240
accacggcgg acgtccgcga cgccgccgac atcctgcgcc cggtcttcga cgccaccgac   300
ggccaggacg gccgggtctc gatcgaggtc gacccgcgcc tggcccacaa caccaaggcg   360
acggtcgccg aggccaagca gctggcctgg ctggtcgacc gccccaacac gctcatcaag   420
atcccggcca ccaaggcggg catcccggcg atcacggcct tcatcggcct cggcatcagc   480
gtcaacgtga cgctgatctt ctcgctcgag cgctaccgca tggtcatgga cgcctacctc   540
gccggcctgg agaaggccaa ggagcgcggc ctggacctgt cgaagatcca ctcggtggcg   600
tccttcttcg tgtcccgcgt ggacaccgag atcgacaagc ggatcgacgc cctcggcacg   660
ccggaggcca aggccgcgcg cggcaaggcg ggcctggcca acgcccggct cgcctacgag   720
gcgtacgagg cggtcttctc caccgaccgc tggctcgccc tcgacaaggc gcaggccaac   780
aagcagcgcc cgctgtgggc ctccaccggc gtcaaggacc cggcgtacaa ggacaccatg   840
tacgtcgagg aactggtcgc gccgaacacc gtgaacacca tgccggaggc cactttggag   900
gccaccgcgg acacggcgga gatccgggc aacaccatcg ccggcacgta cgagcaggcc     960
cgcgccgacc tcgacgccgt cgagaagctc gggatccgcgt gggatcgacgt ggtccagtc   1020
ctggaggaag agggcgtcga caagttcgag gcgtcctgga acgacctgct caagtcgacc   1080
gaggcggagc tccagcgcct cgccccctcg gagggctga                          1119

SEQ ID NO: 16           moltype = DNA  length = 1137
FEATURE                 Location/Qualifiers
source                  1..1137
                        mol_type = other DNA
                        organism = Streptomyces avermitilis
SEQUENCE: 16
atgatcactg tgagcaacac cgtcgaaaac ctcgagcgcc tctccgacga aggcgtctcc     60
atctggctga cgatctgtc gcgcaagcgg atcacgtccg gcaacctcgc cgaactcatc     120
gcgcacaagc acgtggtggg cgtcaccacc aacccgtcca tcttccaggc cgccatcggc   180
tccggagagg gatacgagga gcagctggcc gatctggccg tgcgtggcgt cacggtcgac   240
gaggccgtgc gcatgatgac gaccgccgac gtgcgcgccg ccgccgacat cctgcgggcc   300
gtgtacgacg cgaccggcgg ccgtgacggc cgggtctcca tcgaggtcga cccgcgcctc   360
gcccaccgaca ccgaggcgac gatccgcgaa gccaagcagc tcgcctggct ggtgaccgac   420
cccaacgtga tgatcaagat tccggcgacc aaggccggtc tccccgcgat caccgaggtc   480
atcggcctcg gcatcagcgt caacgtcacg ctgatcttct cgctcgagcg ctaccgcgag   540
gtgatggacg cctacctcgc cggtctggag cgggcgcagg ccgcgggcat cgacctggcc   600
ggcatccact ccgtcgcctc cttcttcgtc tcccgcgtcg acagcgagat cgacaagcgc   660
ctggcgaagg ccggcacgga cgacgcgcag gccctcaagg caaggcggc gctcgccaac   720
gcccggctcg cgtacgaggc gtacgaagag gtcttcgccg gggagcgctg gaccgcgctc   780
gccccggccg gcgcgcacaa gcagcgtccg ctgtgggcct cgacgggcgt gaaggacccg   840
gcgtacaagg acacccgta cgtcgacgag ctggtcgctc ccggcacggt caacaccatg   900
ccggagggca ccttgaacgc caccgccgac cacggcgaca tccacggcga cacggtgacc   960
ggcggctatg cccaggcccg cgccgacctg gccgccgtgg agcggctggg gatctcgtac   1020
gacgaggtcg tgaagcagct ggaggacgag gccgtcgcca agttcgaggt ggcgtgggc   1080
gacctgctgg aggccgtcgc gacctcgctg cgcggcaagg gagctgacgg cgaatga       1137

SEQ ID NO: 17           moltype = DNA  length = 1593
FEATURE                 Location/Qualifiers
source                  1..1593
                        mol_type = other DNA
                        organism = Streptomyces lividans
SEQUENCE: 17
atgtccgagc cggaagagca gcagcccgac atccacacga ccgcgggcaa gctcgcggat     60
ctcaggcgcc gtatcgagga agcgacgcac gccggttccg cacgcgccgt cgagaaacag   120
cacgccaagg gcaagctgac ggctcgtgag cgcatcgacc tcctcctcga cgagggctcc   180
ttcgtcgagc tggacgagtt cgcccggcac cgctccacca acttcggcct cgacgccaa    240
cgcccttacg gcgacggcgt cgtcaccggt tacggcaccg tcgacggccg ccccgtggcc   300
gtcttctccc aggacttcac cgtcttcggc ggcgcgctgg gcgaggtcta cggccagaag   360
atcgtcaagg tgatggactt cgcgctgaag accggctgcc cggtcgtcgg catcaacgac   420
tccgcggcgc cccgcatcca ggagggcgtg gcctccctcg gcgcctacgg cgagatcttc   480
cgccgcaaca cccacgcctc cggcgtgatc ccgcagatca gcctggtcgt cggccgtgc    540
```

-continued

```
gcgggcggcg cggtctactc ccccgcgatc accgacttca cggtgatggt cgaccagacc    600
agccacatgt tcatcaccgg ccccgacgtg atcaagacgg tcaccggtga ggacgtcggc    660
ttcgaggagc tgggcggcgc ccgcacccac aacaccgcct cgggcgtggc ccaccacatg    720
gcgggtgacg agaaggacgc cgtcgagtac gtcaagcagc cctgtcgta cctgccgtcc    780
aacaacctgt ccgagccccc cgccttcccg gaggaggcgg acctcgccgt cacggacgag    840
gacgccgagc tggacgcgat cgtcccggac tcggcgaacc agccctacga catgcacagc    900
gtcatcgagc acgtcctgga cgacggcgag ttcttcgaga cccagcccct gttcgcaccg    960
aacatcctca ccggcttcgg ccgcgtggag ggccgcccgg tcggcatcgt cgccaaccag   1020
cccatgcagt tcgccgggtg cctggacatc accgcctccg agaaggcggc ccgcttcgtg   1080
cgcacctgcg acgccttcaa cgtccccgtg ctcaccttcg tggacgtccc cggcttcctg   1140
cccggcgtcg accaggagca cgacggcatc atccgccgcg cgccaagct gatcttcgcc   1200
tacgccgagg ccacggtgcc gctgatcacg gtcatcaccc gcaaggcctt cggcggcgcc   1260
tacgacgtca tgggctccaa gcacctgggc gccgacctca acctggcctg gccaccgcc   1320
cagatcgcca tcatgggcgc ccagggcgcg tcaacatcc tgcaccgccg caccatcgcc   1380
gacgccggtg acgacgccga ggccaccccg gcccgcctga tccaggagta cgaggacgcc   1440
ctcctcaacc cctacacggc ggccgaacgc ggctacgtcg acgccgtgat catgccctcc   1500
gacactcgcc gccacatcgt ccgcggcctg cgccagctac gcaccaagcg cgagtccctg   1560
cccccgaaga agcacggcaa catcccctg taa                                 1593

SEQ ID NO: 18        moltype = DNA  length = 1599
FEATURE              Location/Qualifiers
source               1..1599
                     mol_type = other DNA
                     organism = Streptomyces avermitilis
SEQUENCE: 18
atgtccgagc cggaagagct gcaccacccc gatatccaca ccaccgcggg caaactcgcg     60
gatctgcagc gccgcatcca ggaggcgacg cacgccggct cggagcgcgc cgtcgaaaag    120
cagcacgcca agggcaagct gacggcccgt gagcggatcg cgctgctgct cgacgaggac    180
tccttcgtcg agctggacga gttcgcgcag caccgctcca cggacttcgg catggagaac    240
aaccgcccgt acggagacgg tgtcgtcacc gggtacggcc cgtcgacgg ccgccccgtc    300
gccgtgttct cgcaggactt caccgtcttc ggcggtgccc tcggcgaggt cttcgggcag    360
aagatcatga aggcgatgga cttcgccctg aagacgggct gtccggtcat cggcatcaac    420
gactccggcg gcgcccgtat ccaggagggc gtctcggccc tcggcatgta cggcgagatc    480
ttccgccgca acacccatgc ctcgggcgtg atcccgcaga tcagcctggt cgtcggcccg    540
tgcgcggccg gcgcggtcta ctccccccgcg atcaccgact tcaccgtgat ggtcgaccag    600
acctcgcaca tgttcatcac ggggcccgac gtcatcaaga cggtgacggg cgaggacgtc    660
ggcttcgagg agctgggcgg cgcccgcacg cacaacgcgg tgtcgggcgt ggcccatcac    720
atggcggggg aggagaagga cgcgatcgag tacgtcaagc agctgctgtc gtacctgccg    780
tccaacaacc tcagcgagcc gccggccttc ccggaggagg cggacctcgc cctcaccgac    840
gaggaccgcg agctggacac cctcgtaccc gacagtgcga accagccgta cgacatgcac    900
acggtgatcg aacacatcct ggacgacgcc gagttcctgg agacgcagcc gctgttcgcg    960
ccgaacatcc tcaccggctt cggccgggtc gagggccacc cggtgggcat cgtcgccaac   1020
cagccgatgc agttcgcggg ctgcctcgac atcacgcgt ccgagaaggc cgcccgcttc   1080
gtgcgcacct gcgacgcgtt caacgtcccg gtgatcactt tcgtggacgt gccgggcttc   1140
ctgcccggtg tcgccagga gcacgacggc atcatccgcc gcggcccaa gctgatctac   1200
gcgtacgccc aggcgaccgt cccgctgatc accgtcatca ccgcaaggc gttcggcggc   1260
ggctacgacg tcatgggctc caagcacctg ggcgccgacc tcaacctgc ctggccgacc   1320
gcccagatcg ccgtgatggg cgcgcagggc gcgtcaaca tcctgcaccg ccgcaccatc   1380
gccgccacac ccgaggagga gcgcgaggag gtccgccggc ggctcatcca ggagtacgag   1440
gacacgctgc tcaaccccta cacggcggcc gagcgcggct acatcgacgg cgtgatcatg   1500
ccgtccgaca cccgcgccca tgtcgtacgg gggctgcgtc agctccgtac gaagcgggaa   1560
tccctgcctc cgaagaagca cggcaacatc ccctctag                            1599

SEQ ID NO: 19        moltype = DNA  length = 1719
FEATURE              Location/Qualifiers
source               1..1719
                     mol_type = other DNA
                     organism = Streptomyces lividans
SEQUENCE: 19
atgaccgtca acgagcccgt acctgacacc ttcgaggaca cccccgcggg ggaccggcac     60
ccggactggt tcaaacgagc cgtcttctac gaggtcctcg tccgctcctt ccaggacagc    120
aacggcgacg catcggtga tctcaagggc ctgaccgcca agctggacta cctgcaatgg    180
ctcggcgtgg actgcctgtg gctcccgccc ttcttcaagt caccgctgcg cgacggcggt    240
tacgacgtct ccgactacac cgccgtgctg ccggagttcg ggacctgcc tgatggcggt    300
gagttcgtgg acgcggcgca ccagcgcggc atgcgcgtga tcatcgactt cgtcatgaac    360
cacaccagcg accagcaccc gtggttccag gagtcccgca agaacccgga cggccctac    420
ggcgactact acgtctgggc cgacgacgac acccggtacg ccgacgcccg catcatcttc    480
gtcgacaccg aggcctccaa ctggacctac gacccgtcc gcggcagta ctactggcac    540
cggttcttct cccaccagtc ggacctcaac tacgaggcc cggcccgtgca gaaggagatg    600
ctcgccgccc tgaagttctg gctggacctg gcgtggacg gctaccgtct cgacgccgtg    660
ccctacctgt acgccgagga gggcaccaac tgcgagaacc tgcccgcctc ccacgcgttc    720
ctcaagcggg tgccgcgcga gatcacgca cagtacccgg acaccgtact gctggccgag    780
gccaaccagt ggcggagga cgtggtcgac tacttcggcg actactccac gggcggcgac    840
gagtgccaca tggcctccaa cttccccgtc atgcccgca tcttcatggc cgtcgccggg    900
gagtcccgct acccggtctc cgaaatcctg ccaagaccc ccgcgatccc gtccggctgc    960
cagtgggca tcttcctgcg caaccacgac gagctgacc tggagatggt caccgacgag   1020
gaacgcgact acatgtacgc ggagtacgcc aaggacccgc gcatgcgcgc caacatcggt   1080
atccgccggc ggctggccac cctgctggac aacgaccgcg accagatcga gctgttcacc   1140
gccctgctgc tcgccctccc gggatccccg atcctctact acggcgacga gatcggcatg   1200
```

```
ggcgacaaca tctggctcgg cgaccgcgac gccgtgcgca cccccatgca gtggacgccc 1260
gaccgcaacg ccggcttctc gacctgtgac ccggggccgcc tctacctgcc cgcgatcatg 1320
gacccggtct acggctacca ggtgacgaac gtcgaggcgt ccatggcctc gccctcctcc 1380
ctgctgcact ggaccggcg catgatcgag atccgcaagc agaacccggc cttcggcctc 1440
ggcacctaca ccgaactgcc ctcctccaac ccggcgcgtg tcgccttcct gcgggagtac 1500
gaggacgacc tggtgctgtg tgtgaacaac ttcgcacggt tcgcccagcc caccgagctg 1560
gatctgcgcg agttcgccgg acgcatccg gtcgagctgt tcggcggggt ccgcttcccc 1620
gccatcggcg aactgccgta cctgctgacc ctcgggggcc acggcttcta ctggttccgg 1680
ctcacccgag tcgcatcccg catcggccgc cgcgcttga                          1719
```

```
SEQ ID NO: 20          moltype = DNA  length = 1752
FEATURE                Location/Qualifiers
source                 1..1752
                       mol_type = other DNA
                       organism = Streptomyces avermitilis
SEQUENCE: 20
atgatcgtca acgagcccgt cccggacacc ttcgaggaca cgcccgccaa ggaccgcgat  60
ccggagtggt tcaaacgcgc cgtcttctac gaggtcctgg tccgctcctt ccaggacagc 120
aacggcgacg gtgtcggcga cctgaaggcc ctgaccgcca agctggacta tctgcagtgg 180
ctgggcgtgg actgcctgtg gctgccgccg ttcttcaagt ccccccctgcg cgacggcggc 240
tacgacgtct ccgactacac cgcggtgctg cccgagttcg gtgacctggc cgacttcgtc 300
gagttcgtgg acgcggccca ccagcgcggc atgcgcggtg tcatcgactt cgtgatgaac 360
cacaccagtg acctgcatcc gtggttccag gagtcccgca gcaacccga cggccctac 420
ggcgactact acgtgtgggc cgacgacgac aagcagtacc aggacgcccg gatcatcttc 480
gtcgacaccg aggcctccaa ctggacgtac gacccggtcc gcaagcagta ctactggcac 540
cgcttcttct cccaccagcc cgacctcaac tacgagaacc tgccgtcca ggaggagatc 600
ctggcggcgc tgcggttctg gctcgatctg ggcatcgacg gcttcaggct ggacgccgtc 660
ccctacctgt acaacgaaga ggggacgaac tgcgagaacc tgccggcgac gcacgagttc 720
ctgaagcggg tgcgcaagga gatcgacacg cactatccgg acacggtgct gctcgcggag 780
gcgaaccagt ggccggagga cgtggtcgac tacttccctc ggggcggcgac 840
gagtgccaca tggcgttcca tttcccggtc atgccgcgga tcttcatggc ggtgcggcgt 900
gagtcgcggt atccggtgtc ggagatcctg gcgaagacgc cggcgatccc gtcgagctgc 960
cagtggggca tcttcctgcg caaccacgac gagctgaccc tggagatggt caccgacgag 1020
gaacgcgact acatgtgggc ggagtacgac aaggatccgc ggatgcggga caacatcggc 1080
atccggcggc gtctggccgc gctgctggac aacgaccgca accagatcga gctgttcacc 1140
gcgctgctgc tgtcgctgcc cggctcgccg atcctctact acggcgacga gatcgggatg 1200
ggggacaaca tctggctcgg tgaccggac gcggtgcgca cgccgatgca gtggacgccc 1260
gaccgcaacg cgggttttctc gtcctgcgac ccggggcgtc tgtatctgcc cacgatcatg 1320
gatccggtct acgggtacca ggtcacgaac gtggaggcgt cgatgtcgtc gccgtcctcg 1380
ctgctgcact ggaccggcg gatgatcgag atccgtaagc agaacccggc gttcggcctc 1440
ggctcgtaca ccgaactcca gtccgaac ccggccgtcc tcgcgttcct gcgggaggcc 1500
ccctcgaccg ggggaacgg ggacgacctg gtgctgtgcg tgcacaactt ctcccggttc 1560
gcgcagccca cggagctgga tctgcagccg ttcagcgacg gtcatccggt cgagctgatc 1620
ggcggtgtcc gcttcccggc catcgggaa ctcccgtatc tgctgaccct ggcaggccac 1680
ggcttctact ggttccggct ccgcaaggac gtcacccagg tcaccaaggt gagcttgttc 1740
gtgagctctt ga                                                     1752
```

```
SEQ ID NO: 21          moltype = DNA  length = 1701
FEATURE                Location/Qualifiers
source                 1..1701
                       mol_type = other DNA
                       organism = Streptomyces lividans
SEQUENCE: 21
atgaccgtca acgagcccgt acctgacacc ttcgaggaca ccccgcggg ggaccggcac  60
ccggagactgg tcaaacgagc cgtcttctac gaggtcctgg tccgctcctt ccaggacagc 120
aacggcgacg gcatcggtga tctcaagggc ctgaccgcca agctggacta cctgcaatgg 180
ctcggcgtgg actgcctgtg gctccccgcc ttcttcaagt caccgctgcg cgacggcggt 240
tacgacgtct ccgactacac cgcggtgctg ccggagttcg gcgacctggc cgacttcgtg 300
gagttcgtgg acgcggcgca ccagcgcggc atgcgcgtga tcatcgactt cgtcatgaac 360
cacaccagcg accagcaccc gtggttccag gagtcccgca ggaacccgga cggccctac 420
ggcgactact acgtctgggc cgacgacgac aagcagttcc aggacgcgcg gatcatcttc 480
gtcgacaccg aggcgtccaa ctggacctac gacccggtgc gcaagcagta ctactggcac 540
cggttcttct cccaccagcc ggacctcaac tacgagaacc cggtcgtgca ggaggagatg 600
atctccggcc tgaagttctg gctggacctg ggcatcgacg ggttccggct ggacgcggta 660
ccgtacctct accaggagga gggcaccaac tgcgagaacc tccgcgcac gcacgacttc 720
ctgaagcggg tgcgcaagga gatcgacgcg cagtacccgg acacggtggt gctcgccgag 780
gccaaccagt ggccggagga cgtggtcgac tacttcggcg actacgcggc gggcggcgac 840
gagtgccaca tggccttcca cttccccgtc atgccccgca tcttcatggc ggtcagaagg 900
gagtcccgct acccggtctc cgaaatcctg gccaagacgc cggccatccc gtccggctgg 960
cagtggggca tcttcctgcg caaccacgac gagctgaccc tggagatggt caccgacgag 1020
gaacgcgact acatgtacgc ggagtacgcc aaggacccgc gcatgcgcgc caacatcggc 1080
atccggcgca ggctcgcccc gctcctcgac aacgaccgca accagatcga gctgttcacc 1140
gccctgctgc tgtccctgcc cggctcgccg atcctctact acggcgacga gatcggcatg 1200
ggcgacaaca tctggctcgg cgaccgcgac gccgtgcgcc cgccgatgca gtggacgccc 1260
gaccgcaacg cgggcttctc gtcgtccgac ccgggccgcc tgttcctgcc cacgatcatg 1320
gaccggggtcc acgttaccac ggtgacgaac gtcgaggcgt ccatggcctc gccctcctcc 1380
ctgctgcact ggaccggcg catgatcgag atccgcaagc agaacgtggc cttcggcctc 1440
ggcacctaca ccgagctgcc gtcgtccaac cctgccgtcc tggccttcct gcgcgaacac 1500
gaggacgacc tggtgctgtg cgtccacaac ttctcccggt tcgcgcagcc gacggagctg 1560
```

```
gacctcagcg ccttcgacgg acgccatccg gtcgagctgt tcggcggggt ccgcttcccg   1620
gcggtcggtg acctgccgta cctgctgacc ctgggcggtc acggcttcta ctggttccgc   1680
ctgcgcaagg acgccgcctg a                                             1701

SEQ ID NO: 22           moltype = DNA  length = 1719
FEATURE                 Location/Qualifiers
source                  1..1719
                        mol_type = other DNA
                        organism = Streptomyces avermitilis
SEQUENCE: 22
atgatcgtca acgagcccgt cccggacacc ttcgaggaca cgcccgccaa ggaccgcgat     60
ccggagtggt tcaaacgcgc cgtcttctac gaggtcctgg tccgctcctt ccaggacagc    120
aacggcgacg gtgtcggcga cctgaagggc ctgaccgcca agctggacta tctgcagtgg    180
ctgggcgtgg actgcctgtg gctgccgccg ttcttcaagt cccccctgcg cgacggcgtg    240
tacgacgtct ccgactacac cgcggtgctg cccgagttcg gtgacctggc cgacttcgtg    300
gagttcgtgg acgcggccca ccagcgcggc atgcgcgtga tcatcgactt cgtgatgaac    360
cacaccagcg acctgcaccc gtggttccag gagtcccgca gcaaccccga cggccctac     420
ggcgactact acgtgtgggc cgacgacgac aagcagtacc aggagcccg gatcatcttc     480
gtcgacaccg aggcctccaa ctggaccttc gacccggtcc gcaagcagta ctactggcac    540
cgcttcttct cccaccagcc cgacctcaac tacgagaacc cggcggtgca ggaggagatc    600
gtctccgccc tgcggttctg gctcgacctc ggcatcgacg gcttccgcct cgacgcggtg    660
ccgtacctgt accagcagga aggcaccaac tgcgagaacc tgccggcgac gcacgagttc    720
ctgaagcggg tgcgcaagga gatcgacacg cactatccgg acacggtgct gctcgcggag    780
gcgaaccagt ggccgaggag cgtggtcgac tacttcggcg acttcccctc gggcggcgac    840
gagtgccaca tggcgttcca tttcccggtc atgccgcgga tcttcatggc ggtgcggcgt    900
gagtcgcggt atccggtgtc ggagatcctg gcgaagacgc tcgagctgg                960
cagtggggca tcttcctgcg caaccacgac gagctgaccc tggagatggt caccgacgag   1020
gaacgcgact acatgtgggc ggagtacgcc aaggatccgc ggatgcgggc caacatcggc   1080
atccgccggc gtctggcgcc gctgctgaac aacgaccgca accagatcga gctgttcacc   1140
gcgctgcctgc tgtcgctgcc cggctcgccg atcctctact acggcgacga gatcggcatg   1200
ggggacaaca tctggctcgg tgaccgggac gcggtgcgca ctccgatgca gtggacgccg   1260
gaccgcaacg cgggtttctc gtcctgcgac ccggggcgtc tgtatctgcc cacgatcatg   1320
gatccggtct acgggtacca ggtcacgaac gtggaggcgt cgatgtcgtc gccgtcctcg   1380
ctgctgcact ggaccgggcg gatgatcgag atccgtaagc agaacccggc gttcggcctc   1440
ggctcgtaca ccgaactcca gtcctcgaac ccggccgtcc tcgcgttcct ggcggaggcc   1500
ccctcgaccg gggggaacgg ggacgacctg tgtcgtgcg tgcacaactt ctccggttc    1560
gcgcagccca cggagctgga tctgcgggcg ttcagcggcc gtcatccggt cgagctgatc   1620
ggcggtgtcc gcttcccggc catcgggaa ctcccgtatc tgctgaccct ggcaggccac    1680
ggcttctact ggttccggct ccgcaaggac gccgtctag                         1719

SEQ ID NO: 23           moltype = DNA  length = 2115
FEATURE                 Location/Qualifiers
source                  1..2115
                        mol_type = other DNA
                        organism = Streptomyces lividans
SEQUENCE: 23
gtgttcatgc aggtctggcc tggagaggcg tatccactgg gtgccacgta cgacggcgcc    60
ggcaccaact tcgcggtctt cacggaggcc gccgacgag tagagctgtg tctgctgcac    120
gacgacggtt cggagacggc ggtcgagctg cgggagagcg atgccttcgt gcggcacgcg    180
tacgtgccgg gcgtgatgcc ggggcagcgg tacggctacc gcgtgcacgg cccgtacgcc    240
ccggagcgcg gactcgcctg caacagcgcc aagctgctcc tcgatccgta tcgcgcgttg    300
atcagcgggg aggtccagtg gggcgaggag gtgtacggct accacttcgg cgcacccgaa    360
cggcgcaacg acctcgactc ggccccgcac acgatgacgt cggtcgtggt caacccgtac    420
ttcgactggg gcgacgaccg gcgccccgt acggagtacc accacggt gatctacgag      480
gcccacgtga agggcctgac catgcgccac ccgggccacg aggagcg gcggggcacc     540
tacgcggccc tcgcgcaccc ggcgctcatc gagcacctca cggggctcgg gtgaccgcg   600
ctggagctga tgccggtcca tcagttcgtc aacgaccacc ggctggtgga catgggcctc   660
aacaactact ggggctacaa cacggtcggg ttcttcgccc cgcacaacgc ctacgcctcc   720
tggggcgacc gcggccagca ggtgctggag ttcaagtccg cggtcaaggc gctgcacgag   780
gcggggatcg aggtgatcct cgacgtggtc tacaaccaca ccgcggaggg caaccacctg   840
ggcccgacgc tgtccttcaa ggggctggac aaccctcgt actaccggct ggccgacgac    900
ccccgctact acatggacac cacggggacc gggaactcgc tgctcatgcg gtcccgcac   960
gtactccaga tgatcatgga ctcactgcgg tactgggtca ccgagatgca cgtggacggg   1020
ttccgtttcg acctcgcggc cacgctggcc cggcagttcc acgaggtgga ccggctgtcg   1080
tcgttcttcg acctggtgca gcaggaccc gtggtctcgc aggtgaagct gatcgccgag   1140
ccgtgggacg tgggcagggg cggctaccag gtgggcaact tccgccgct gtgaccgag   1200
tggaacggca agtaccggga cacggtgcgg gacctgtggc gcggcgagcc gcgcacgctg   1260
gcggagttcg cgtcccggct gaccggttcc tccgacctct accaggacga cggccgcgc   1320
ccgctggcct cgatcaactt cgtgacctgc cacgacggtc tcaccctgca acatggggtg   1380
gcctacaacg acaagcacaa ccacgccaac ggcgaggaca accgggacgg cgagagccac   1440
aaccgttcct ggaactgcgg tgtcgagggc gacaccgacg atccggcgt gctggagctg   1500
cgggcgcggc agatgcgcaa cttcatcgcc acgctgctgc tctcccaggg cgtcccgatg   1560
ctcagccacg gcgacgagtt cgcccgcacc cagcggggca caacaacgc ctactgccag   1620
gacaacgac tggcgtgggt ggcgggccc gaggacggcc acgacctct ggagttcacc     1680
cgcgcgatgt tctggctgcg caaggaccac ccggtcctgc gcaggcgccg cttcttccac   1740
gggcgcccgt gcagggcac ccacgacgag ctgtcggaca tcgcctggtt cacgccggag   1800
ggcgcggaga tgcccagcg ggactggaac tcggcacggg cctccgcgct cacggtcttc   1860
ctgaacggca acgcgatctc cgagcccggc accgcgggga acgcatcgc cgacgattcg   1920
ttcctgctga tgttcaacgc cgcgccgagg ccgctggact tcgtggtgcc ggtcgatcac   1980
```

```
ggccggcagt gggaggtggt cgtcgacacc gctctgacgg ccggggtgcc cacgggcacg  2040
ggcccgaagg tgcaggccgg ggaccggctg accctcctgg accggagcct gacggtgttg  2100
cagcggccgg tgtag                                                   2115

SEQ ID NO: 24           moltype = DNA  length = 2109
FEATURE                 Location/Qualifiers
source                  1..2109
                        mol_type = other DNA
                        organism = Streptomyces avermitilis
SEQUENCE: 24
atgcaggtct ggcctggaga ggcatatcca ctcggcgcca cgtacgacgg cgccggtacc   60
aatttcgcgg tcttctcgga ggccgcccat cggatcgagc tgtgtctgct gcacgacgac  120
ggctcggaga cggcggtgga actgagggag accgacgcgt tcgtgcgcca cgcgtatctg  180
cccggcgtca tgccggggca gcggtacggc ttccgcgtgc acggcccgtt gcgcgcggac  240
cgcggggtgc gctgcaattc cgccaagctg ctgctcgatc cgtacgcgaa ggcgatcagc  300
ggcgagatca agtgggcga ggaggtgtac ggctaccact tcggcgcccc cgacaagcgc   360
aacgacctgg actcggcgcc gcacacgatg acctcggtcg tgatcaaccc gtacttcgac  420
tggggcaacg accggcggcc gcgcaccgag taccaccaca cagtgctcta cgaggcccat  480
gtgaagggcc tgacgatgcg cgatcccgcg ctgcccgagg aactgcgcgg cacgtatgcg  540
gcgctcgccc accccgccat catcgaacac ctgactgaac tgggcgtcac cgcgctcgaa  600
ctgatgccga tgcaccagtt cgtgaacgac caccgtctgg tggacatggg cctgaacaac  660
tactggggct acaacacgat cggttttctc gccccgcaca acgctacgc tcctgggcg    720
gaccgcggcc agcaggtgct ggagttcaag tcggcagtga aggcgctgca cgaggccggg  780
atcgaggtca tcctggacgt ggtctacaag cacacggccg agggcaacca catgggcccg  840
acgtctcct tcaagggcat cgacaacgcg tcgtactacc ggctcaccga cgatcccgc   900
tactacatgg acaccacggg gacgggaac tccctcctca tgcgctcccc gcacgtcctc   960
caactgatca tggactcgct gcgctactgg gtcagcgaca tgcatgtcga cggcttccgg 1020
ttcgacctcg cggccaccct ggcccggcag ttccacgagg tggaccggct gtcgtcgttc 1080
ttcgacctgg tccagcagga cccggtggtc tccaggtga agctgatcgc cgagccgtgg  1140
gacgtcggcg agggcggcta ccaggtgggc aacttcccgc cctgtgggac cgagtggaac 1200
ggcaagtacc gcgacacggt gcgggacatg tggcggggcg agccgcgtac gctcgcggag 1260
ttcgcctccc gcctgacggg ctcgtcggac ctctaccagg acgacggccg ccgtcccctc 1320
gcctccatca acttcgtcac ctgccacgac ggtttcaccc tgcacgacct cgtcgcgtac 1380
aacgacaagc acaaccaggc caacgccgag gacaaccggg acggggagag ccacaaccgg 1440
tcctggaact gcggggcgga gggcgacacc gacgatccgg cggtgctggc ggttgcgggcg 1500
cgccagatgc gcaacttcat cgccacgctg atgctctcgc agggcgtgcc gatgctcagc 1560
cacggggatg agttcgcgcg cacccagggc ggcaacaaca acgcgtactg ccaggacggc 1620
gagctgtcgt gggtggcgtg gcccgaggac ggcagcgagc tgctggagtt cacgcgcgcg 1680
atggtggtgc tgccggcgca ccatccggtc ttccggcgc gccgcttctt ccacgggcgg 1740
ccggtggagg gcacgcacga cgagctgtcg gacatcgtct ggttcacgcc gacgggtgag 1800
gagatgatcc agcgcgactg ggattcgcg caggcacggg cgctgacggt gttcctcaac  1860
ggcaccgcga tctccgagcc cggcccacg ggagagcgga tctcggacga ctccttcctg 1920
ttgatgttca acgcctcccc gaagtcgctg gagttcgtgg tgccggtcga ccacggccgg 1980
cagtggcagg tcgtcgtcga cacggcacgc acgacggaga tcccgccggg cacggtcgcg 2040
aaggtcaagg ccggggaccg gctgacgctg gtggaccgga gcctcacggt gttgcagcgg 2100
ccggcctga                                                         2109

SEQ ID NO: 25           moltype = DNA  length = 30
FEATURE                 Location/Qualifiers
misc_feature            1..30
                        note = Primer
source                  1..30
                        mol_type = other DNA
                        organism = synthetic construct
SEQUENCE: 25
aagatcccgg tcttcgaggc gggcaagggc                                    30

SEQ ID NO: 26           moltype = DNA  length = 30
FEATURE                 Location/Qualifiers
misc_feature            1..30
                        note = Primer
source                  1..30
                        mol_type = other DNA
                        organism = synthetic construct
SEQUENCE: 26
gcggcgtagg tgtcggtctt cgacttgggg                                    30

SEQ ID NO: 27           moltype = DNA  length = 28
FEATURE                 Location/Qualifiers
misc_feature            1..28
                        note = Primer
source                  1..28
                        mol_type = other DNA
                        organism = synthetic construct
SEQUENCE: 27
caaaggccgc aacaacaccc tctccgcc                                      28

SEQ ID NO: 28           moltype = DNA  length = 26
FEATURE                 Location/Qualifiers
```

```
misc_feature         1..26
                     note = Primer
source               1..26
                     mol_type = other DNA
                     organism = synthetic construct
SEQUENCE: 28
tagcccgcgc agaacgcctc ccggca                                   26

SEQ ID NO: 29        moltype = DNA  length = 26
FEATURE              Location/Qualifiers
misc_feature         1..26
                     note = Primer
source               1..26
                     mol_type = other DNA
                     organism = synthetic construct
SEQUENCE: 29
cccaggatga gcccctcgag gcgcag                                   26

SEQ ID NO: 30        moltype = DNA  length = 29
FEATURE              Location/Qualifiers
misc_feature         1..29
                     note = Primer
source               1..29
                     mol_type = other DNA
                     organism = synthetic construct
SEQUENCE: 30
ctgatcgtgc tgctgctgat gacgtacga                                29

SEQ ID NO: 31        moltype = DNA  length = 30
FEATURE              Location/Qualifiers
misc_feature         1..30
                     note = Primer
source               1..30
                     mol_type = other DNA
                     organism = synthetic construct
SEQUENCE: 31
tccgccgacc tggccggctc gaacaacacc                               30

SEQ ID NO: 32        moltype = DNA  length = 30
FEATURE              Location/Qualifiers
misc_feature         1..30
                     note = Primer
source               1..30
                     mol_type = other DNA
                     organism = synthetic construct
SEQUENCE: 32
gccagccggc cgcgtactgt ccgcggacgg                               30
```

METHOD FOR PRODUCING SEDOHEPTULOSE

RELATED APPLICATION

This application is a divisional of U.S. application Ser. No. 17/049,789 filed Oct. 22, 2020, allowed, which is a national stage of PCT/JP2019/017832 filed Apr. 26, 2019 and claims the benefit of priority of application number 2018-087503 filed with the Japan Patent Office on Apr. 27, 2018. The contents of the priority application is incorporated herein by reference.

REFERENCE TO SEQUENCE LISTING

In accordance with 37 CFR § 1.833-1835 and 37 CFR§ 1.77(b)(5), the specification makes reference to a Sequence Listing submitted electronically as a .xml file named "549562US_ST26.xml". The .xml file was generated on Aug. 23, 2023 and is 56,884 bytes in size. The entire contents of the Sequence Listing are hereby incorporated by reference.

TECHNICAL FIELD

The present invention relates to a method for producing sedoheptulose by a bacterium, a method for improving the productivity of sedoheptulose by the bacterium, and the bacterium for the methods.

Background

Sedoheptulose, which is a saccharide falling within the categories of ketoses and heptuloses, is one of a small number of heptuloses occurring in nature. Sedoheptulose is a constituent sugar of D-sedoheptulose-7-phosphate in the pentose phosphate pathway, which is a metabolic system of a living organism. A method using a bacterium has been reported as a method for producing sedoheptulose. So far, it has been reported that *Streptomyces naraensis* (Patent literatures 1-2 and non-Patent literature 1), *Streptomyces albus* (non-Patent literature 1 and Patent literature 3), *Streptomyces californicus* (non-Patent literature 1 and Patent literature 3), *Streptomyces sindensis* (non-Patent literature 1), *Streptomyces olivaceus* (non-Patent literature 1), *Streptomyces vividochromogenus* (non-Patent literature 1), and *Flavobacterium* sp. TSC-A, *Achromobacter* sp. TSC-B (Patent literature 4) can produce sedoheptulose as the bacterium. In the above-mentioned literatures, bacteria that produce sedoheptulose in the natural world have been reported, but no method for improving the productivity of sedoheptulose in these bacteria is known. It is known that an addition of ribose to *Bacillus subtilis* mutated in transketolase improves the productivity of sedoheptulose (maximum production is 25 g/L, production is 5 g/L when ribose is absent) (Patent literature 5). As a method for producing sedoheptulose other than using a bacterium, methods using transketolase (Non-patent literatures 2 and 3) and a method by chemical synthesis (Patent literature 6) have been reported.

PRIOR ART DOCUMENTS

Patent Literatures

[Patent literature 1] JP S39-14500 B
[Patent literature 2] JP S41-4400 B
[Patent literature 3] JP S41-5915 B
[Patent literature 4] JP S41-21760 B
[Patent literature 5] JP S62-126990 A
[Patent literature 6] SK284318

Non-Patent Literatures

[Non-patent literature 1] Accumulation of sedoheptulose by Streptomycetes. J. Biochem. 1963; 54(1):107-8
[Non-patent literature 2] An efficient synthesis of sedoheptulose catalyzed by Spinach Transketolase, Tetrahedron Asymmetry. 1993; 4: 1169-1172
[Non-patent literature 3] Heptulose synthesis from nonphosphorylated aldoses and ketoses by Spinach transketolase, J. Biol chem. 1971 25; 246(10):3126-31.
[Non-patent literature 4] Crystal structures and mutational analyses of Acyl-CoA carboxylase p subunit of *Streptomyces coelicolor*. Biochemistry 2010; 49(34):7367-7376
[Non-patent literature 5] Subinhibitory concentrations of antibiotics induce phenazine production in a marine *Streptomyces* sp. J Nat Prod. 2008 May; 71(5):824-827

SUMMARY OF INVENTION

Problems to be Solved by the Invention

A problem to be solved by the present invention is to provide a method for producing sedoheptulose by a bacterium, a method for improving the productivity of sedoheptulose by the bacterium, and the bacterium for the methods.

Means for Solving the Problem

The present invention provides:
(1) a method for producing sedoheptulose, including culturing a bacterium in which a function of transaldolase is deleted or attenuated;
(2) the method according to (1), where the bacterium is a bacterium in which a function of propionyl CoA carboxylase or a function of trehalose synthase is further deleted or attenuated;
(3) the method according to (1) or (2), where the bacterium is actinomycete, *Bacillus subtilis*, a bacterium belonging to *Flavobacterium*, or a bacterium belonging to *Achromobacter;*
(4) the method according to (3), where the bacterium is actinomycete;
(5) the method according to (4), where the actinomycete is a bacterium belonging to *Streptomyces;*
(6) the method according to (5), where the bacterium belonging to *Streptomyces* is *Streptomyces lividans* or *Streptomyces avermitilis;*
(7) a bacterium in which a function of transaldolase and a function of propionyl CoA carboxylase or a function of trehalose synthase are deleted or attenuated;
(8) the bacterium according to (7), where the bacterium is actinomycete, *Bacillus subtilis*, a bacterium belonging to *Flavobacterium*, or a bacterium belonging to *Achromobacter.*
(9) the bacterium according to (8), where the bacterium is actinomycete;

(10) the bacterium according to (9), where the bacterium is a bacterium belonging to *Streptomyces*; or

(11) the bacterium according to (10), where the bacterium is *Streptomyces lividans* or *Streptomyces avermitilis*.

Effect of the Invention

The present invention provides a method for producing sedoheptulose by a bacterium, a method for improving the productivity of sedoheptulose by the bacterium, and the bacterium for the methods.

MODES FOR CARRYING OUT THE INVENTION

Figure 1:
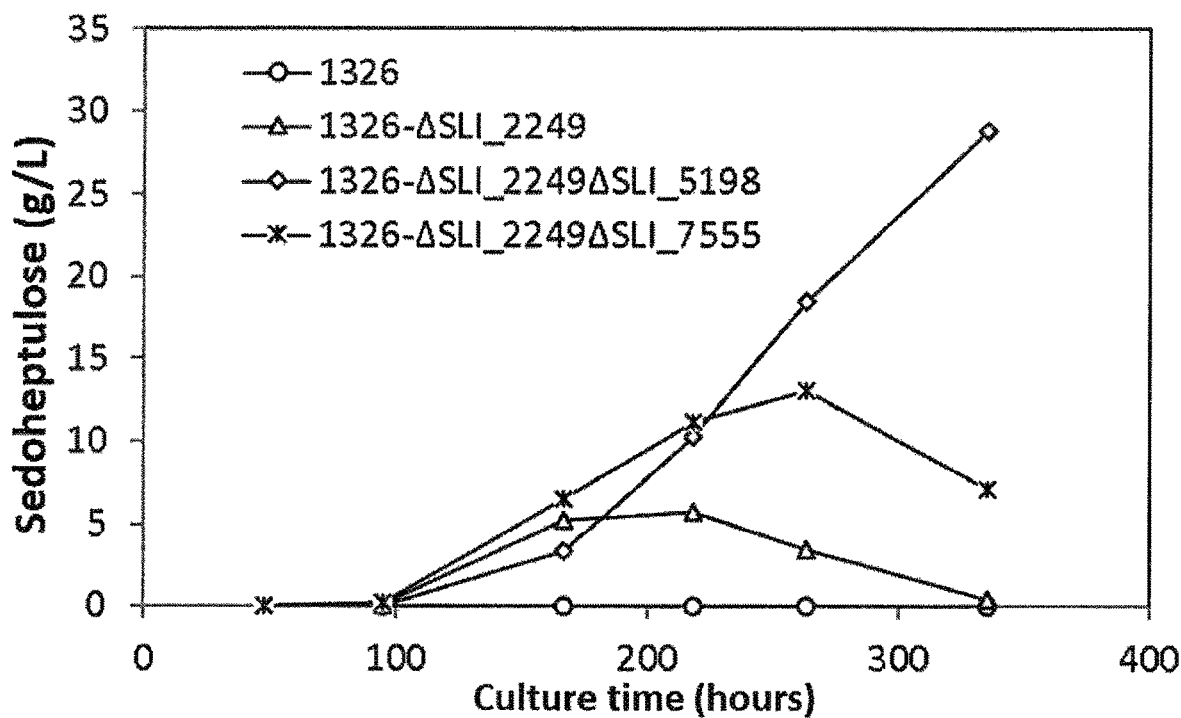
FIG. 1 shows the results of the production of sedoheptulose using *Streptomyces lividans* strain 1326.

In one aspect, the present invention relates to a method for producing sedoheptulose, including culturing a bacterium in which the function of transaldolase is deleted or attenuated.

In another aspect, the present invention relates to a bacterium in which a function of transaldolase is deleted or attenuated.

In yet another aspect, the present invention relates to a method for improving a productivity of sedoheptulose, including culturing a bacterium in which a function of transaldolase is deleted or attenuated.

In the present disclosure, sedoheptulose refers to sedoheptulose represented by the molecular formula $C_7H_{14}O_7$. For sedoheptulose, D-type and L-type are not particularly limited, but sedoheptulose is preferably D-sedoheptulose.

In the present disclosure, transaldolase enables to catalyze a reaction of converting sedoheptulose-7-phosphate and glyceraldehyde-3-phosphate to erythrose-4-phosphate and fructose-6-phosphate, and the reaction is reversible. Transaldolase is, for example, SLI_2249 (SEQ ID NO: 1) and SLI_7007 (SEQ ID NO: 2) for *Streptomyces lividans* and sav6314 (SEQ ID NO: 3) and sav1767 (SEQ ID NO: 4) for *Streptomyces avermitilis*.

[Sequence 1]
(SEQ ID NO: 1)
MTDALKRLSDEGVAIWLDDLSRKRITSGNLAELIDQQHVV

GVTTNPSIFQKAISQGDGYDQGLADLAVRGVTVEEAIRMI

TTADVRDAADILRPVYDNTGGKDGRVSIEVDPRLAHNTHA

TVAEAKQLAWLVDRPNTFIKIPATEAGLPAIAETIGLGIS

VNVTLIFSLERYRKVMDAFLTGLEKAKERGLDLSQIHSVA

SFFVSRVDTEIDKRIDALGTDEAKAQRGKAAVANARLAYQ

AYEEVFGTDRWAALEKAGANKQRPLWASTGVKDKAYSDTM

YVTDLVAPNTVNTMPEATLLATEDHGEITGDAVAGSYERA

RADLDAIEKLGISYDEVVQLLEKEGVDKFEDAWNDLLKST

EAELKRLAPSKG

[Sequence 2]
(SEQ ID NO: 2)
MITVTEATATAGALQRLADQGVSVWLDDLSRRRIESGNLA

ELIRTKNVVGVTTNPSIFQAAIGSGEGYEEQLADLATRGV

TVDEAVRMMTTADVRAAADVLRGVYDASGGRDGRVSIEVD

PRLAHDTAATVAEARQLSWLVDRPNVMIKIPATKAGLPAI

TEVIGAGISVNVTUFSLERYREVMDAYLAGLEKAGAAGID

LAGINSVASFFVSRVDSEIDKRLSLLGTEEALGLRGRAAL

ANARLAYEAYENVFAGDRFTALAGARANPQRPLWASTGVK

DPAFRDTLYVEELVAPGTVNTMPEATLDAAADHGDVRGDT

VTGGYAQARADLAAVERLGVSYDEVVEQLEQEGVAKFEAA

WQELLAAVTKSLQSKGVDGE

[Sequence 3]
(SEQ ID NO: 3)
MTDALKRLSKEGVAIWLDDLSRKRITSGNLAELIDQQHVV

GVTTNPSIFQKAISQGDGYDQQVSDLAARRVIVEEAIRMI

TTADVRDAADILRPVFDATDGQDGRVSIEVDPRLAHNTKA

TVAEAKQLAWLVDRPNTLIKIPATKAGIPAITEVIGLGIS

VNVTUIFSLERYRMVMDAYLAGLEKAKERGLDLSKIHSVA

SFFVSRVDTEIDKRIDALGTPEAKAARGKAGLANARLAYE

AYEAVFSTDRWLALDKAQANKQRPLWASTGVKDPAYKDTM

YVEELVAPNTVNTMPEATLEATADHGEIRGNTIAGTYEQA

RADLDAVEKLGIAYDDVVQLLEEEGVDKFEASWNDLLKST

EAELQRLAPSEG

[Sequence 4]
(SEQ ID NO: 4)
MITVSNTVENLERLSDEGVSIWLDDLSRKRITSGNLAELI

AHKHVVGVTTNPSIFQAAIGSGEGYEEQLADLAVRGVTVD

EAVRMMTTADVRAAADILRPVYDATGGRDGRVSIEVDPRL

AHDTEATIAEAKQLAWLVDRPNVMIKIPATKAGLPAITEV

IGLGISVNVTLIFSLERYREVMDAYLAGLERAQAAGIDLA

GIHSVASFFVSRVDSEIDKRLAKAGTDDAGALKGKAALAN

ARLAYEAYEEVFAGERWTALAPAGAHKQRPLWASTGVKDP

AYKDTLYVDELVAPGTVNTMPEGTLNATADHGDIHGDTVT

GGYAQARADLAAVERLGISYDEVVKQLEDEAVAKFEVAWG

DLLEAVATSLRGKGADGE

In the present disclosure, propionyl CoA carboxylase may catalyze a carboxylation reaction of propionyl CoA to produce methylmalonyl CoA. Propionyl CoA carboxylase is, for example, SLI_5198 (SEQ ID NO: 5) and sav_3331 (SEQ ID NO: 6). Propionyl CoA carboxylase is also known as an enzyme involved in the synthesis of secondary metabolites (Non-patent literature 4).

[Sequence 5]
(SEQ ID NO: 5)
MSEPEEQQPDIHTTAGKLADLRRRIEEATHAGSARAVEKQ
HAKGKLTARERIDLLLDEGSFVELDEFARHRSTNFGLDAN
RPYGDGVVTGYGTVDGRPVAVFSQDFTVFGGALGEVYGQK
IVKVMDFALKTGCPVVGINDSGGARIQEGVASLGAYGEIF
RRNTHASGVIPQISLVVGPCAGGAVYSPAITDFTVMVDQT
SHMFITGPDVIKTVTGEDVGFEELGGARTHNTASGVAHHM
AGDEKDAVEYVKQLLSYLPSNNLSEPPAFPEEADLAVTDE
DAELDAIPDSANQPYDMHSVIEHVLDDGEFFETQPLFAPN
ILTGFGRVEGRPVGIVANQPMQFAGCLDITASEKAARFVR
TCDAFNVPVLTFVDVPGFLPGVDQEHDGIIRRGAKLIFAY
AEATVPLITVITRKAFGGAYDVMGSKHLGADLNLAWPTAG
IAVMGAQGAVNILHRRTIADAGDDAEATRARLIQEYEDAL
LNPYTAAERGYVDAVIMPSDTRRHIVRGLRQLRTKRESLP
PKKHGNIPL

[Sequence 6]
(SEQ ID NO: 6)
MSEPEELHHPDIHTTAGKLADLQRRIQEATHAGSERAVEK
QHAKGKLTARERIALLLDEDSFVELDEFAQHRSTDFGMEN
NRPYGDGVVTGYGTVDGRPVAVFSQDFTVFGGALGEVFGQ
KIMKAMDFALKTGCPVIGINDSGGARIQEGVSALGMYGEI
FRRNTHASGVIPQISLVVGPCAGGAVYSPAITDFTVMVDQ
TSHMFITGPDVIKTVTGEDVGFEELGGARTHNAVSGVAHH
MAGEEKDAIEYVKQLLSYLPSNNLSEPPAFPEEADLALTD
EDRELDTLVPDSANQPYDMHTVIEHILDDAEFLETQPLFA
PNILTGFGRVEGHPVGIVANQPMQFAGQLDIDASEKAARF
VRTCDAFNVPVITFVDVPGFLPGVGQEHDGIIRRGAKLIY
AYAEATVPLITVITRKAFGGAYDVMGSKHLGADLNLAWPT
AQIAVMGAQGAVNILHRRTIAATPEEEREEVRRRLIQEYE
DTLLNPYTAAERGYIDGVIMPSDTRAHVVRGLRQLRTKRE
SLPPKKHGNIPL In the present disclosure, trehalose synthase may synthesize trehalose from glucose. The trehalose synthase is, for example, SLI_7555 (SEQ ID NO: 7), sav_7396 (SEQ ID NO: 8), SLI_5710 (SEQ ID NO: 9), sav_2803 (SEQ ID NO: 10) and SLI_6475 (SEQ ID NO: 11) and sav_2151 (SEQ ID NO: 12).

[Sequence 7]
(SEQ ID NO: 7)
MTVNEPVPDTFEDTPAGDRHPDWFKRAVFYEVLVRSFQDS
NGDGIGDLKGLTAKLDYLQWLGVDCLWLPPFFKSPLRDGG
YDVSDYTAVLPEFGDLADFVEFVDAAHQRGMRVIIDFVMN
HTSDQHPWFQESRKNPDGPYGDYYVWADDDTRYADARIIF
VDTEASNWTYDPVRGQYYWHRFFSHQPDLNYENPAVQEEM
LAALKFWLDLGVDGYRLDAVPYLYAEEGTNCENLPASHAF
LKRVRREIDAQYPDTVLLAEANQWPEDVVDYFGDYSTGGD
ECHMAFHFPVMPRIFMAVRRESRYPVSEILAKTPAIPSGC
QWGIFLRNHDELTLEMVTDEERDYMYAEYAKDPRMRANIG
IRRRLATLLDNDRDGIELFTALLLALPGSPILYYGDEIGM
GDNIWLGDRDAVRTPMQWTPDRNAGFSTCDPGRLYLPAIM
DPVYGYQVTNVEASMASPSSLLHWTRRMIEIRKQNPAFGL
GTYTELPSSNPAVLAFLREYEDDLVLCVNNFARFAQPTEL
DLREFAGRHPVELFGGVRFPAIGELPYLLTLGGHGFYWFR
LTRVASRIGRRA

[Sequence 8]
(SEQ ID NO: 8)
MIVNEPVPDTFEDTPAKDRDPEWFKRAVFYEVLVRSFQDS
NGDGVGDLKGLTAKLDYLQWLGVDCLWLPPFFKSPLRDGG
YDVSDYTAVLPEFGDLADFVEFVDAAHQRGMRVIIDFVMN
HTSDLHPWFQESRSNPDGPYGDYYVWADDDKQYQDARIIF
VDTEASNWTYDPVRKQYYWHRFFSHQPDLNYESAAVQEEI
LAALRFWLDLGIDGFRLDAVPYLYNEEGTNCENLPATHEF
LKRVRKEIDTHYPDTVLLAEANQWPEDVVDYFGDFPSGGD
ECHMAFHFPVMPRIFMAVRRESRYPVSEILAKTPAIPSSC
QWGIFLRNHDELTLEMVTDEERDYMWAEYAKDPRMRANIG
IRRRLAPLLQNDRNQIELFTALLLSLPGSPILYYGDEIGM
GDNIWLGDRDAVRTPMQWTPDRNAGFSSCDPGRLYLPTIM
DPVYGYQVTNVEASMSSPSSLLHWTRRMIEIRKQNPAFGL
GSYTELQSSNPAVLAFLREAPSTGGNGDDLVLCVHNFSRF
AQPTELDLRAFSGRHPVELIGGVRFPAIGELPYLLTLAGH
GFYWFRLRKDVTQVTKVSLFVSS

[Sequence 9]
(SEQ ID NO: 9)
MTVNEPVPDTFEDTPAGDRHPDWFKRAVFYEVLVRSFQDS
NGDGIGDLKGLTAKLDYLQWLGVDCLWLPPFFKSPLRDGG
YDVSDYTAVLPEFGDLADFVEFVDAAHQRGMRVIIDFVMN
HTSDQHPWFQESRRNPDGPYGDYYVWADDDKQFQDARIIF
VDTEASNWTYDPVRKQYYWHRFFSHQPDLNYENPVVQEEM
ISALKFWLDLGIDGFRLDAVPYLYQEEGINCENLPRTHDF
LKRVRKEIDAQYPDTVVLAEANQWPEDVVDYFGDYAAGGD
ECHMAFHFPVMPRIFMAVRRESRYPVSEILAKTPAIPSGC
QWGIFLRNHDELTLEMVTDEERDYMYAEYAKDPRMRANIG
IRRRLAPLLQNDRNQIELFTALLLSLPGSPILYYGDEIGM
GDNIWLGDRDAVRTPMQWTPDRNAGFSSSDPGRLFLPTIM
DPVHGYQVTNVEASMASPSSLLHWTRRMIEIRKQNVAFGL

```
GTYTELPSSNPAVLAFLREHEDDLVLCVHNFSRFAQPTEL

DLSAFDGRHPVELFGGVRFPAVGDLPYLLTLGGHGFYWFR

LRKDAA
```

[Sequence 10]
(SEQ ID NO: 10)
```
MIVNEPVPDTFEDTPAKDRDPEWFKRAVFYEVLVRSFQDS

NGDGVGDLKGLTAKLDYLQWLGVDCLWLPPFFKSPLRDGG

YDVSDYTAVLPEFGDLADFVEFVDAAHQRGMRVIIDFVMN

HTSDLHPWFQESRSNPDGPYGDYYVWADDDKQYQDARIIF

VDTEASNWTFDPVRKQYYWHRFFSHQPDLNYENPAVQEEI

VSALRFWLDLGIDGFRLDAVPYLYQQEGTNCENLPATHEF

LKRVRKEIDTHYPDTVLLAEANQWPEDVVDYFGDFPSGGD

ECHMAFHFPVMPRIFMAVRRESRYPVSEILAKTPAIPSSC

QWGIFLRNHDELTLEMVTDEERDYMWAEYAKDPRMRANIG

IRRRLAPLLQNDRNQIELFTALLLSLPGSPILYYGDEIGM

GDNIWLGDRDAVRTPMQWTPDRNAGFSSCDPGRLYLPTIM

DPVYGYQVTNVEASMSSPSSLLHWTRRMIEIRKQNPAFGL

GSYTELQSSNPAVLAFLREAPSTGGNGDDLVLQVHNFSRF

AQPTELDLRAFSGRHPVELIGGVRFPAIGELPYLLTLAGH

GFYWFRLRKDAV
```

[Sequence 11]
(SEQ ID NO: 11)
```
VFMQVWPGEAYPLGATYDGAGTNFAVFTEAADRVELCLLH

DDGSETAVELRESDAFVRHAYVPGVMPGQRYGYRVHGPYA

PERGLRQNSAKLLLDPYARAISGEVQWGEEVYGYHFGAPE

RRNDLDSAPHTMTSVVVNPYFDWGDDRRPRTEYHHTVIYE

AHVKGLTMRHPGLPEELRGTYAALAHPALIEHLTGLVTA

LELMPVHQFVNDHRLVDMGLNNYWGYNTVGFFAPHNAYAS

WGDRGQQVLEFKSAVKALHEAGIEVILDVVYNHTAEGNHL

GPTLSFKGLDNPSYYRLADDPRYYMDTTGTGNSLLMRSPH

VLQMIMDSLRYWVTEMHVDGFRFDLAATLARQFHEVDRLS

SFFDLVQQDPVVSQVKLIAEPWDVGEGGYQVGNFPPLWTE

WNGKYRDTVRDLWRGEPRTLAEFASRLTGSSDLYQDDGRR

PLASINFVTCHDGFTLHDMVAYNDKHNHANGEDNRDGESH

NRSWNCGVEGDTDDPAVLELRARQMRNFIATLLLSQGVPM

LSHGDEFARTQRGNNNAYCQDNELAWVAWPEDGHDLLEFT

RAMVWLRKDHPVLRRRRFFHGRPVQGTHDELSDIAWFTPE

GAEMAQRDWNSARASALTVFLNGNAISEPGTRGERIADDS

FLLMFNAAPRPLDFVVPVDHGRQWEVVVDTALTAGVPTGT

GPKVQAGDRLTLLDRSLTVLQRPV
```

[Sequence 12]
(SEQ ID NO: 12)
```
MQVWPGEAYPLGATYDGAGTNFAVFSEAAHRIELCLLHDD

GSETAVELRETDAFVRHAYLPGVMPGQRYGFRVHGPFAPG

RGVRCNSAKLLLDPYAKAISGEIKWGEEVYGYHFGAPDKR

NDLDSAPHTMTSVVINPYFDWGNDRRPRTEYHHTVLYEAH

VKGLTMRHPALPEELRGTYAALAHPAIEHLTELGVTALEL

MPVHQFVNDHRLVDMGLNNYWGYNTIGFFAPHNAYASWGD

RGQQVLEFKSAVKALHEAGIEVILDVVYNHTAEGNHMGPT

LSFKGIDNASYYRLTDDPRYYMDTTGTGNSLLMRSPHVLQ

LIMDSLRYWVSDMHVDGFRFDLAATLARQFHEVDRLSSFF

DLVQQDPVVSQVKLIAEPWDVGEGGYQVGNFPPLWTEWNG

KYRDTVRDMWRGEPRTLAEFASRLTGSSDLYQDDGRRPLA

SINFVTCHDGFTLHDLVAYNDKHNGANGEDNRDGESHNRS

WNCGAEGDTDDPAVLALRARQMRNFIATLMLSQGVPMLSH

GDEFARTQGGNNNAYCQDGELSWVAWPEDGSELLEFTRAM

VWLRRDHPVFRRRRFFHGRPVEGTHDELSDIVWFTPTGEE

MIQRDWDSAQARALTVFLNGTAISEPGPRGERISDDSFLL

MFNASPKSLEFVVPVDHGRQWQVWDTARTDGIPPGTVAKV

KAGDRLTLVDRSLTVLQRPA
```

As a specific example, the DNA sequences encoding SEQ ID NO: 1-12 are SEQ ID NO: 13-24, respectively.

[Sequence 13]
(SEQ ID NO: 13)
```
ATGACAGACGGACTCAAGGGGCTCTCCGATGAAGGCGTGG

GGATCTGGCTGGACGACCTGTCGCGCAAGCGGATCACGTC

CGGCAACCTCGCCGAGCTGATCGACCAGCAGCACGTCGTG

GGCGTCACCACCAACCCGTCGATCTTCCAGAAGGCCATCT

CGCAGGGCGACGGCTACGACCAGCAGCTCGCCGACCTCGC

CGTCCGCGGAGTCACGGTCGAAGAGGCCATCCGCATGATC

ACCACGGCGGACGTCCGCGACGCCGCCGACATCCTGCGCC

CCGTCTACGACAACACCGGCGGCAAGGACGGCCGGGTCTC

CATCGAGGTGGACCCGGGGCTGGCGCACAACACCCACGCC

ACGGTGGCCGAGGCCAAGCAGCTGGCGTGGCTGGTGGACC

GGCCGAACACCTTCATCAAGATCGGGGCGACCGAGGGGGG

CCTGCCGGCCATCGCCGAGACCATCGGCCTGGGCATCAGC

GTCAACGTCACGCTGATCTTGTCCCTGGAGGGGTAGGGGA

AGGTCATGGACGCCTTCCTGACCGGCCTGGAGAAGGCCAA

GGAGCGTGGCGTGGACCTCTCGCAGATCCACTCCGTGGCG

TGCTTCTTCGTGTCCCGCGTGGACACCGAGATCGAGAAGC

GGATCGACGGGCTCGGCACCGACGAGGCCAAGGCGCAGCG

CGGCAAGGGGGGGGTCGCCAAGGGGGGGGTGGCCTACCAG
```

-continued

GCGTAGGAGGAGGTCTTCGGCACCGACCGCTGGGCCGCCC

TGGAGAAGGCCGGCGCCAACAAGCAGCGTCCGCTGTGGGC

GTCGACCGGTGTGAAGGACAAGGCGTACAGCGACACCATG

TACGTCACCGACCTGGTCGCGCCGAACACGGTCAACACCA

TGCCGGAGGCCACGCTGCTGGCCACCGAGGACCACGGCGA

GATCACCGGCGACGCCGTCGCCGGGTCGTACGAGCGGGCC

CGCGGGGACCTCGACGCGATCGAGAAGCTCGGGATCTCCT

ACGACGAGGTGGTCCAGCTCCTGGAGAAGGAAGGCGTCGA

CAAGTTCGAGGACGCCTGGAACGACCTGCTGAAGTCCACG

GAGGCGGAGCTCAAGCGCCTCGCTCCCTCGAAGGGCTGA

[Sequence 14]
(SEQ ID NO: 14)
ATGATCACTGTGACCGAAGCAACCGCCACCGGGGGAGCAC

TGCAGCGCCTGGCCGACCAGGGCGTGTCCGTCTGGGTCGA

CGACGTGTCGCGGGGGGGGATCGAGTCCGGCAACCTCGCC

GAGCTGATCAGGACGAAGAACGTCGTCGGAGTCACCACCA

ACCCGTCGATCTTCCAGGCCGCCATAGGCTCCGGCGAGGG

CTACGAGGAGCAGCTCGCCGACCTGGCGACGGGGGGGGTC

ACCGTCGACGAGGGGGTCCGCATGATGACCACCGCCGATG

TCCGCGCCGCCGCCGACGTGCTGCGCGGGGTGTACGACGC

CTCCGGGGGCGCGACGGCCGCGTCTCCATCGAGGTCGACC

CGCGCCTGGCCCACGAGACGGCGGCGACGGTCGCCGAGGC

CCGCCAGCTGTCCTGGCTGGTCGACCGTCCCAACGTGATG

ATGAAGATCCCGGCGACGAAGGCCGGTCTCCCGGCCATCA

CCGAGGTCATCGGCGCCGGCATCAGTGTGAACGTCACGCT

GATCTTCTCCCTGGAGCGCTAGCGCGAGGTCATGGACGCC

TACCTCGCCGGCCTGGAGAAGGCGCAGGCGGCCGGGATCG

AGCTGGCCGGCATCCACTCGGTCGCGTCCTTCTTCGTCTC

CCGCGTCGACAGCGAGATCGACAAGCGCCTGTCCCTGCTG

GGCACCGAAGAGGCGCTCGGCCTGCGCGGCCGGGGGCAC

TGGCCAACGCACGACTGGCCTACGAGGCGTACGAGAACGT

CTTCGGGGGCGACCGCTTCACCGCCCTCGCGGGGGCCCGC

GCGAACCCCCAGGGCCCCCTGTGGGCGTCCACCGGTGTGA

AGGACCCGGCATTCCGGGACACCCTGTACGTGGAGGAGCT

GGTCGCCCCCGGGACCGTGAACACGATGCCGGAGGCCACC

CTGGACGCCGCCGCCGATCACGGCGACGTACGGGGGGACA

CGGTCACCGGGGGGTACGCCCAGGCCCGCGCCGATCTCGC

GGCCGTGGAGCGGCTCGGCGTGTCGTACGACGAGGTGGTG

GAGCAGTTGGAGGAGGAGGGGGTGGCGAAGTTCGAGGGGG

CCTGGCAGGAGGTGCTCGCCGCCGTGACGAAGTCCCTCGA

GAGGAAGGGAGTTGACGGGGAATGA

[Sequence 15]
(SEQ ID NO: 15)
ATGACAGACGCACTCAAGCGCCTCTCCAAGGAAGGCGTCG

CGATCTGGCTGGACGACCTGTCGCGCAAGCGGATCACGTC

CGGCAACCTCGCCGAACTGATCGACCAGCAGCACGTCGTG

GGCGTCACCACCAACCCGTCGATCTTCCAGAAGGCCATCT

CTCAGGGCGACGGTTACGACCAGCAGGTCTCCGACCTCGC

CGCCCGCCGGGTCACCGTCGAAGAAGCCATCCGCATGATC

ACCACGGCGGACGTCCGCGACGCCGCCGACATCCTGCGCC

CGGTCTTCGACGCCACCGACGGCCAGGACGGCCGGGTCTC

GATCGAGGTCGACCCGCGCCTGGCCCACAACACCAAGGCG

AGGGTCGCCGAGGCCAAGCAGCTGGCCTGGGTGGTCGACC

GCCCCAACACGCTCATCAAGATCCCGGCCACCAAGGGGGG

CATCCCGGCGATCACGGAGGTCATCGGCCTCGGCATCAGC

GTCAACGTGACGCTGATCTTCTCGCTCGAGCGCTACCGCA

TGGTCATGGACGCCTACCTCGCCGGCGTGGAGAAGGCCAA

GGAGCGCGGCCTGGACCTGTCGAAGATCCACTCGGTGGCG

TCCTTCTTCGTGTCCCGCGTGGACACCGAGATCGAGAAGC

GGATCGACGCCCTCGGCACGCCGGAGGCCAAGGCCGCGCG

CGGCAAGGGGGCCTCGCCAACGCCCGGCTCGCCTACGAG

GCGTAGGAGGGGTCTTCTCGACCGACCGCTGGCTCGCCC

TCGAGAAGGCGCAGGCCAACAAGCAGCGCCCGCTGTGGGC

CTCCACCGGCGTCAAGGACCCGGCGTACAAGGACACCATG

TACGTCGAGGAACTGGTCGCGCCGAACACCGTGAACACCA

TGCCGGAGGCCACTTTGGAGGCCACCGCGGACCACGGCGA

GATCCGGGGCAACACCATCGCCGGCACGTACGAGCAGGCC

CGCGCCGACCTCGACGCCGTCGAGAAGCTCGGGATCGCGT

ACGACGACGTGGTCCAGCTCCTGGAGGAAGAGGGCGTCGA

CAAGTTCGAGGCGTCCTGGAACGACCTGCTCAAGTCGACC

GAGGCGGAGCTCCAGCGCCTCGCCCCCTCGGAGGGCTGA

[Sequence 16]
(SEQ ID NO: 16)
ATGATCAGTGTGAGCAACACCGTCGAAAACCTCGAGCGCC

TCTCCGACGAAGGCGTCTCCATCTGGCTGGAGGATCTGTC

GCGCAAGCGGATCACGTCGGGCAACCTCGCCGAACTCATC

GCGCACAAGCAGGTGGTGGGCGTCACCACCAACCCGTCCA

TCTTCCAGGCCGCCATCGGCTCCGGAGAGGGATACGAGGA

GCAGCTGGCCGATGTGGCCGTGCGTGGCGTCACGGTCGAC

GAGGGGGTGCGCATGATGACGACCGCCGACGTGGGGGGGG

CCGCCGACATCCTGGGGGGGGTGTAGGACGCGACCGGGGG

CCGTGACGGCCGGGTGTCCATCGAGGTCGACGGGGGCGTC

GCCCACGACACCGAGGCGACGATCGCCGAAGCCAAGCAGC

TCGCCTGGCTGGTGGACCGCCCCAACGTGATGATCAAGAT

-continued

TCCGGCGACCAAGGCCGGTCTCCCCGCGATCACCGAGGTC

ATCGGCCTCGGCATCAGCGTCAACGTCACGCTGATCTTCT

CGCTCGAGCGCTACCGCGAGGTGATGGACGCCTACCTCGC

CGGTCTGGAGCGGGGCAGGCCGCGGGCATCGACCTGGCC

GGCATCCACTCCGTCGCCTCCTTCTTCGTCTCCCGCGTCG

ACAGCGAGATCGACAAGCGCCTGGCGAAGGGGGGCACGGA

CGACGCGCAGGCCCTGAAGGGCAAGGCGGCGCTCGCCAAC

GCCCGGCTCGCGTACGAGGGGTACGAAGAGGTCTTCGCCG

GGGAGCGCTGGACCGCGCTCGCCCCGGCCGGCGCGCACAA

GCAGCGTCCGCTGTGGGCCTCGACGGGGGTGAAGGACCCG

GCGTACAAGGACACCCTGTACGTCGACGAGCTGGTCGCTC

CGGGCACGGTCAACACCATGCCGGAGGGGACCTTGAAGGC

CACCGCCGACCACGGCGACATCCACGGCGAGACGGTGACC

GGGGGCTATGCCCAGGCGCGCGCGGACCTGGCCGCCGTGG

AGCGGCTGGGGATCTCGTAGGACGAGGTCGTGAAGGAGCT

GGAGGACGAGGGGGTCGCCAAGTTCGAGGTGGGGGGGGCG

ACCTGCTGGAGGCCGTCGCGACCTCGCTGCGCGGCAAGGG

AGCTGACGGCGAATGA

[Sequence 17]

(SEQ ID NO: 17)
ATGTCCGAGCCGGAAGAGCAGCAGCCCGACATCCACACGA

CCGCGGGCAAGCTCGCGGATCTCAGGCGCCGTATCGAGGA

AGCGACGCACGCCGGTTCCGCACGCGCCGTCGAGAAACAG

CACGCCAAGGGCAAGCTGACGGCTCGTGAGCGCATCGACC

TCCTCCTCGACGAGGGCTCCTTCGTCGAGCTGGACGAGTT

CGCCCGGCACCGCTCCACCAACTTCGGCCTCGACGCCAAC

CGCCCTTACGGCGACGCGTCGTCAGGGGTTACGGCACCG

TCGAGGGGGCCCCGTGGCCGTCTTCTCCCAGGACTTCAC

CGTCTTGGGGGGGCGCTGGGGGAGGTCTACGGCCAGAAG

ATCGTCAAGGTGATGGACTTCGCGCTGAAGAGGGGCTGCC

CGGTCGTCGGCATCAACGACTCGGGGGGCGCCCGCATCCA

GGAGGGCGTGGCCTCCCTCGGCGCCTAGGGCGAGATCTTC

CGCCGCAACACCGACGCCTGGGGGGTGATCCCGGAGATGA

GCGTGGTCGTCGGCCCCGTGCGCGGGGGGCGCGGTCTACTC

CCCCGCGATCACCGACTTCAGGGTGATGGTCGACCAGACC

AGCCACATGTTCATCACCGGCCCCGACGTCATCAAGACGG

TCACCGGTGAGGACGTCGGCTTCGAGGAGCTGGGGGGGGC

CCGCACCCACAACACCGCCTCGGGCGTGGCCCACCACATG

GCGGGTGACGAGAAGGACGCCGTCGAGTACGTCAAGGAGG

TCCTGTCGTACCTGCCGTCCAACAACCTGTCCGAGCCCCC

CGCCTTCCCGGAGGAGGGGACCTCGCGGTCACGGACGAG

-continued

GACGCCGAGCTGGACGCGATCGTCCCGGACTCGGCGAACC

AGCCCTACGACATGCACAGCGTCATCGAGCACGTCCTGGA

CGACGGCGAGTTCTTCGAGACCCAGCCCCTGTTCGCACCG

AACATCCTGACCGGCTTGGGGGGCGTGGAGGGGGGGCGG

TCGGCATCGTCGCCAACCAGCCCATGCAGTTCGCCGGGTG

CGTGGACATGACCGCCTCCGAGAAGGGGGGGGGCTTCGTG

CGCACCTGCGACGCCTTCAACGTCCCCGTGCTCACCTTCG

TGGACGTCCCCGGCTTCCTGCCCGGCGTCGACCAGGAGCA

CGACGGCATCATCCGCCGGGGGGCCAAGCTGATCTTCGCC

TACGCCGAGGCCACGGTGCCGCTGATCACGGTCATCACCC

GCAAGGCCTTCGGGGGCGCCTACGACGTCATGGGCTCCAA

GCACCTGGGGGCCGACCTCAACCTGGCCTGGCCCACCGCC

CAGATCGCCGTCATGGGCGCCCAGGGCGCGGTCAACATCC

TGCACCGCCGCACCATCGCCGACGCCGGTGACGACGCCGA

GGCGACCCGGGCCCGCCTGATCCAGGAGTACGAGGACGCC

CTCCTCAACCCCTAGACGGCGGCCGAAGGGGGGTAGGTCG

AGGGGGTGATCATGGCCTCCGACACTCGCCGCCAGATCGT

CCGCGGCCTGCGCGAGCTACGCACCAAGCGCGAGTCCGTG

CCCCCGAAGAAGCACGGCAACATCCCCCTGTAA

[Sequence 18]

(SEQ ID NO: 18)
ATGTCCGAGCCGGAAGAGCTGCACCACCCCGATATCCACA

CCACCGCGGGCAAACTCGCGGATCTGGAGCGCCGCATCCA

GGAGGCGACGGACGCCGGCTCGGAGCGCGCCGTCGAAAAG

CAGGACGCCAAGGGCAAGGTGACGGCCCGTGAGCGGATCG

CGCTGCTGCTCGACGAGGACTCCTTCGTCGAGCTGGACGA

GTTCGCGCAGCACCGCTCCACGGACTTCGGCATGGAGAAC

AACCGCCCGTACGGAGACGGTGTCGTCACCGGGTACGGGA

CCGTGGACGGCCGCCCCGTCGCCGTGTTCTCGGAGGACTT

CACCGTCTTCGGGGGTGCCCTCGGCGAGGTCTTCGGGCAG

AAGATCATGAAGGCGATGGACTTCGCCCTGAAGACGGGCT

GTCCGGTCATCGGCATCAACGACTCCGGGGGCGCCCGTAT

CCAGGAGGGCGTGTCGGCCCTGGGCATGTAGGGGGAGATC

TTGCGCCGCAACACCCATGCCTCGGGCGTGATCCCGCAGA

TCAGCCTGGTCGTCGGCCCGTGCGGGGGGGCGCGGTGTA

CTCCCCCGCGATCACCGACTTCACGGTGATGGTCGACCAG

ACCTCGCACATGTTCATCACGGGCCCCGACGTCATCAAGA

CGGTGAGGGGGAGGACGTCGGCTTCGAGGAGCTGGGGGG

GGGGGGCACGGAGAACGCGGTGTGGGGGGTGGCCCATCAC

ATGGCGGGGAGGAGAAGGACGCGATCGAGTACGTGAAGC

AGCTGCTGTCGTACCTGCCGTCCAAGAACCTCAGCGAGCC

GCCGGCCTTCCCGGAGGAGGCGGACCTCGCCCTCACCGAC

-continued

GAGGACCGCGAGCTGGACACCCTCGTACCCGACAGTGCGA

ACCAGCCGTACGAGATGCACAGGGTGATCGAACACATCCT

GGACGACGCCGAGTTCCTGGAGACGCAGCCGCTGTTCGCG

CCGAACATCGTCACGGGCTTCGGCGGGTCGAGGGGGACC

CGGTGGGCATCGTCGCCAACCAGCCGATGCAGTTCGGGGG

CTGCCTCGACATCGACGCGTCCGAGAAGGCCGCCCGCTTC

GTGCGCACCTGGGACGCGTTCAACGTCCCGGTGATCACTT

TCGTGGACGTGCCGGGCTTCCTGCCCGGTGTCGGGGAGGA

GCACGACGGCATCATGGGGGGGGGGGGAAGCTGATGTAG

GGGTACGCCGAGGCGACCGTGGGGGTGATGACCGTGATCA

CCCGGAAGGGGTTGGGGGGGCGTACGACGTCATGGGCTC

GAAGCACCTGGGGGGGGACCTCAACCTCGCCTGGCCGACG

GGCCAGATCGCCGTGATGGGCGCGCAGGGGGGGGTCAACA

TCCTGCACCGCCGCACCATCGCCGCCACACCCGAGGAGGA

GCGCGAGGAGGTCCGCCGGCGGCTCATCCAGGAGTACGAG

GACACGCTGCTCAACCCCTACACGGGGGGGGAGGGGGCT

AGATCGACGGCGTGATCATGCCGTCCGAGAGCCGCGCCCA

TGTCGTAGGGGGCTGCGTCAGGTCCGTACGAAGCGGGAA

TCCCTGCCTCCGAAGAAGCACGGCAACATCCCCCTCTAG

[Sequence 19]
(SEQ ID NO: 19)
ATGACCGTCAACGAGCCCGTACCTGACACCTTCGAGGACA

CCCCCGCGGGGACCGGCACCCGGACTGGTTCAAACGAGC

CGTGTTCTACGAGGTCCTCGTCCGCTCCTTCCAGGACAGC

AACGGCGACGGCATCGGTGATCTCAAGGGCCTGACCGCCA

AGCTGGACTACCTGCAATGGCTCGGCGTGGACTGCCTGTG

GCTCCCGCCCTTCTTCAAGTCACCGCTGCGCGACGGGGGT

TAGGACGTCTCCGACTACACCGCCGTGCTGCCGGAGTTCG

GCGACCTGGCCGACTTCGTGGAGTTCGTGGACGCGGCGCA

CCAGCGCGGCATGGGCGTGATCATCGACTTCGTCATGAAC

CACACCAGCGACCAGCACCCGTGGTTCCAGGAGTCCCGCA

AGAACCCGGACGGCCCCTACGCGACTACTACGTCTGGGC

CGACGACGAGACCCGGTACGCCGACGCCCGCATCATCTTC

GTCGACACCGAGGCCTCCAACTGGACCTACGACCCGGTCC

GCGGCCAGTACTACTGGCACCGGTTCTTCTCCCACCAGCC

GGACCTCAACTACGAGAACCCGGCCGTGCAGGAGGAGATG

CTCGCCGCCCTGAAGTTCTGGCTGGACCTGGGCGTGGACG

GCTACCGTCTCGACGCCGTGCCCTACCTGTAGGCCGAGGA

GGGCACCAACTGCGAGAACCTGCCCGCCTCCCACGCGTTC

CTCAAGCGGGTGCGCCGCGAGATCGACGCACAGTACCCGG

ACACCGTACTGCTGGCCGAGGCCAACCAGTGGCCGGAGGA

CGTGGTCGACTACTTCGGCGACTACTCCAGGGGGGGGGAC

GAGTGCGACATGGCCTTCCACTTCCCCGTCATGCCCCGGA

TCTTGATGGCCGTGGGGGGGAGTCCCGGTACCCGGTCTC

CGAAATCCTCGCCAAGACCCCCGCGATCCCGTCGGCTGC

CAGTGGGCATCTTCCTGCGCAACCACGACGAGCTGACCG

TGGAGATGGTCACCGACGAGGAACGCGACTACATGTACGC

GGAGTAGGCCAAGGACCCGCGCATGCGCGCCAACATCGGT

ATCCGCCGGCGGCTGGCCACCCTGCTGGACAACGACCGCG

ACCAGATCGAGCTGTTCACCGCCCTGCTGCTCGCCCTCCC

GGGATCCCCGATCCTCTACTACGGCGACGAGATCGGCATG

GGCGACAACATCTGGCTCGGCGACCGCGACGCCGTGCGCA

CCCCCATGGAGTGGACGCCCGACCGCAACGCCGGCTTCTC

GACCTGTGACCCGGGCCGCCTCTACCTGCCCGCGATCATG

GACCCGGTCTACGGCTACCAGGTGACGAACGTCGAGGCGT

CCATGGCCTCGCCCTCCTCCCTGCTGCACTGGACCCGGCG

CATGATCGAGATCCGCAAGCAGAACCCGGCCTTCGGCCTC

GGCACCTACACCGAACTGCCCCTCCAACCGGGGGGTGC

TCGCCTTCCTGCGGGAGTACGAGGACGACCTGGTGCTGTG

TGTGAACAACTTCGCACGGTTCGCCCAGCCCACCGAGCTG

GATCTGCGCGAGTTCGCCGGACGCCATCCGGTCGAGCTGT

TCGGGGGGTCCGCTTCCCCGCCATCGGCGAACTGCCGTA

CCTGCTGACCCTCGGGGGCCACGGCTTCTACTGGTTCCGG

CTCACCCGAGTCGCATCCCGCATCGGCCGCCGCGCTTGA

[Sequence 20]
(SEQ ID NO: 20)
ATGATCGTCAACGAGCCCGTCCCGGACACCTTCGAGGAGA

GGGGGGGGAAGGACCGCGATCCGGAGTGGTTCAAACGCGC

CGTGTTCTACGAGGTCCTGGTCCGCTCCTTCCAGGACAGG

AACGGCGACGGTGTCGGCGACCTGAAGGGGCTGACCGCCA

AGCTGGACTATGTGCAGTGGCTGGGCGTGGACTGCCTGTG

GCTGCCGCCGTTCTTCAAGTCCCCCCTGCGCGAGGGGGGC

TACGACGTGTCCGACTACACCGGGGTGCTGCCCGAGTTCG

GTGACCTGGCCGACTTCGTCGAGTTCGTGGACGCGGCCCA

CCAGGGGGGCATGCGCGTGATCATCGACTTCGTGATGAAC

CACACCAGTGAGCTGCATCCGTGGTTCGAGGAGTCCCGCA

GCAACCCCGACGGCCCTAGGGCGACTACTACGTGTGGGC

CGACGACGACAAGCAGTACCAGGACGCCCGGATCATCTTC

GTCGACACCGAGGCCTCCAACTGGACGTAGGACCCGGTCC

GCAAGCAGTACTACTGGCACCGCTTCTTGTCCCACCAGCC

CGACCTCAACTACGAGAGTGCCGCCGTCAGGAGGAGATC

CTGGCGGCGCTGGGGTTCTGGCTCGATGTGGGCATCGACG

GCTTCAGGCTGGACGCCGTCCCCTAGCTGTACAACGAAGA

-continued

GGGGACGAACTGCGAGAACCTGCCGGCGACGCACGAGTTC

CTGAAGGGGGGGGAAGGAGATCGACACGCACTATCGGGA

GACGGTGCTGCTCGCGGAGGCGAAGCAGTGGGGGAGGAC

GTGGTCGACTACTTGGGCGACTTCCCCTGGGGGGGGACG

AGTGCCAGATGGCGTTCCATTTCCCGGTCATGCCGGGGAT

CTTCATGGGGGTGCGGGTGAGTCGCGGTATCCGGTGTCG

GAGATCCTGGGGAAGACGCCGGCGATCCCGTCGAGCTGCC

AGTGGGGATCTTCCTGCGCAACCACGACGAGCTGACCCT

GGAGATGGTCACCGACGAGGAAGGGGACTACATGTGGGGG

GAGTAGGCCAAGGATCCGCGGATGGGGGCCAAGATGGGCA

TCCGCCGGGGTCTGGCGCCGCTGGTGGAGAAGGACCGCAA

CCAGATCGAGCTGTTCAGGGGGCTGCTGGTGTCGCTGCCC

GGCTCGCCGATCCTCTACTAGGGGAGGAGATGGGGATGG

GGGACAACATCTGGGTCGGTGAGGGGACGGGGGGGACG

CCGATGCAGTGGACGCCGGACCGCAACGCGGGTTTCTCGT

CCTGCGACCCGGGGGGTCTGTATGTGCCCACGATGATGGA

TCCGGTGTACGGGTACCAGGTCACGAACGTGGAGGCGTCG

ATGTCGTCGCCGTCCTCGCTGCTGCACTGGACCCGGCGGA

TGATCGAGATCCGTAAGGAGAACCCGGCGTTCGGCCTCGG

CTCGTACACCGAACTCCAGTCCTCGAACCCGGCCGTCGTC

GCGTTCCTGGGGGAGGGGGCCTCGACCGGGGGGAACGGGG

ACGACCTGGTGCTGTCGTGCAGAAGTTCTCCCGGTTCGC

GCAGGCCACGGAGCTGGATCTGCGGGGGTTCAGCGGGGGT

CATGGGGTCGAGCTGATCGGCGGTGTCGGCTTCGGGGCCA

TCGGGGAACTCCCGTATCTGCTGACCCTGGCAGGCCACGG

CTTCTACTGGTTCCGGCTCCGCAAGGACGTCACCCAGGTC

ACCAAGGTGAGCTTGTTCGTGAGCTCTTGA

[Sequence 21]
(SEQ ID NO: 21)
ATGACCGTCAACGAGCCCGTACCTGACACCTTCGAGGACA

CCCCCGCGGGGACCGGCACCCGGACTGGTTGAAACGAGC

CGTCTTCTACGAGGTCCTCGTCCGCTCCTTCCAGGACAGC

AACGGCGACGGCATCGGTGATCTCAAGGGCCTGACCGCCA

AGCTGGACTACCTGCAATGGCTCGGCGTGGACTGCCTGTG

GCTCGCGCCCTTCTTCAAGTCACCGCTGGGCGACGGGGT

TAGGACGTCTCCGACTACACCGCCGTGCTGCCGGAGTTCG

GCGACCTGGCCGACTTCGTGGAGTTCGTGGACGCGGCGCA

CCAGCGCGGCATGCGCGTGATCATCGACTTCGTCATGAAC

CACACCAGCGACCAGCACCCGTGGTTCCAGGAGTCCCGCA

GGAACCCGGACGGCCCCTACGCGACTACTACGTCTGGGC

CGACGACGACAAGCAGTTCCAGGAGGGGGGATCATCTTCG

TCGACACCGAGGCGTCCAACTGGACCTACGACCCGGTGCG

CAAGCAGTACTACTGGCACCGGTTCTTCTCCCACCAGCCG

GACCTCAACTACGAGAACCCGGTCGTGCAGGAGGAGATGA

TCTCCGCGCTGAAGTTCTGGCTGGACCTGGGCATCGACGG

GTTCCGGCTGGACGCGGTGCCGTACCTCTACCAGGAGGAG

GGCACCAACTGCGAGAACCTCCCGCGCACGCACGACTTCC

TGAAGCGGGTGCGCAAGGAGATCGACGCGCAGTACCCGGA

CACGGTGGTGCTGGCCGAGGCCAACCAGTGGCCGGAGGAC

GTGGTCGACTACTTCGGCGACTACGGGGGGGGGGGACGA

GTGCCACATGGCCTTCCACTTCCCCGTCATGCCCCGCATC

TTCATGGCGGTCAGAAGGGAGTCCCGCTACCCGGTCTCCG

AAATCCTCGCCAAGACCCCGGCCATCCCGTCCGGCTGCCA

GTGGGGCATCTTCCTGCGGAACCACGACGAGCTGACCCTG

GAGATGGTCACCGACGAGGAAGGGGACTACATGTACGCGG

AGTACGCGAAGGACCCGCGCATGCGCGCCAACATCGGCAT

CCGGCGCAGGCTCGCCCCGCTCCTCGAGAACGACCGCAAC

CAGATCGAGCTGTTGACCGCCCTGCTGCTGTCCGTGCCCG

GCTGGGGGATCCTCTACTACGGCGACGAGATCGGGATGGG

GGACAACATCTGGCTCGGCGACCGCGAGGGCGTGCGCACC

CCCATGCAGTGGAGGCCCGACCGGAAGGGGGGCTTCTCGT

CGTCCGACGGGGGCCGCCTGTTCCTGCCCACGATCATGGA

CCCGGTCCACGGTTACCAGGTGACGAACGTCGAGGCGTCC

ATGGCCTCGCCCTCCTCCCTGCTGCACTGGACCCGGCGCA

TGATCGAGATCCGCAAGCAGAACGTGGCCTTCGGCCTGGG

CACCTACACCGAGCTGCCGTCGTCCAACCCTGCCGTCCTG

GCCTTCCTGCGCGAACACGAGGACGACCTGGTGCTGTGCG

TCCACAACTTCTCCCGGTTCGCGCAGCCGACGGAGGTGGA

CCTCAGCGCCTTCGACGGACGCCATCCGGTCGAGCTGTTC

GGGGGGGTCCGCTTCCCGGCGGTCGGTGACCTGCCGTACC

TGCTGACCCTGGGGGGTCACGGCTTCTACTGGTTCCGCCT

GCGCAAGGACGCCGCCTGA

[Sequence 22]
(SEQ ID NO: 22)
ATGATCGTCAACGAGCCCGTCCCGGACACCTTCGAGGAGA

GGGGGGGGAAGGACCGCGATCCGGAGTGGTTCAAAGGGGG

GGTGTTCTACGAGGTCGTGGTCCGCTCCTTCCAGGACAGG

AAGGGCGACGGTGTCGGCGACCTGAAGGGGCTGACCGCCA

AGCTGGAGTATCTGGAGTGGGTGGGCGTGGACTGCCTGTG

GCTGCCGCCGTTCTTCAAGTCCCCCCTGCGCGAGGGCGGC

TACGACGTCTCCGACTACACCGCGGTGCTGCCCGAGTTCG

GTGACCTGGCCGACTTCGTCGAGTTCGTGGACGCGGCCCA

CCAGGGGGGCATGCGCGTGATCATCGACTTCGTGATGAAC

-continued

CACACCAGCGACCTGCACCCGTGGTTCCAGGAGTCCCGCA

GCAACCCCGACGGCCCCTACGGCGACTACTACGTGTGGGC

CGACGACGACAAGCAGTACCAGGACGCCCGGATCATCTTC

GTCGACACCGAGGCCTCCAACTGGACCTTCGACCCGGTCC

GCAAGCAGTACTACTGGCACCGCTTCTTCTCCCACCAGCC

CGACCTCAACTACGAGAACCCGGGGGTGCAGGAGGAGATC

GTCTCCGCCCTGCGGTTCTGGCTCGACCTCGGCATCGACG

GCTTCCGCCTCGACGCGGTGCCGTACCTGTACCAGCAGGA

AGGCACCAACTGCGAGAACCTGCCGGCGACGGACGAGTTC

CTGAAGCGGGTGCGGAAGGAGATCGACACGCACTATCCGG

ACACGGTGCTGCTCGCGGAGGCGAAGCAGTGGGGGGAGGA

CGTGGTCGACTACTTCGGCGACTTCCCCTCGGGGGGCGAC

GAGTGCCACATGGCGTTCCATTTCGGGGTCATGCCGGGGA

TCTTCATGGGGGTGGGGGGTGAGTCGCGGTATCCGGTGTC

GGAGATCCTGGGGAAGAGGGGGGGGATCCCGTCGAGCTGC

GAGTGGGGCATCTTCCTGCGCAACCACGACGAGCTGACCC

TGGAGATGGTCACCGACGAGGAACGCGACTACATGTGGGC

GGAGTACGCCAAGGATCCGCGGATGCGGGCCAACATCGGC

ATCCGCCGGCGTCTGGCGCCGCTGCTGGACAACGACCGCA

ACCAGATCGAGCTGTTCACCGCGCTGCTGCTGTCGCTGCC

CGGCTCGCCGATCCTCTACTACGGCGACGAGATCGGCATG

GGGGACAACATCTGGCTGGGTGACCGGGACGCGGTGCGCA

CTCCGATGCAGTGGACGCCGGACCGCAACGCGGGTTTCTC

GTCCTGCGACCCGGGGGTCTGTATCTGCCCACGATGATG

GATCCGGTGTACGGGTACCAGGTCACGAACGTGGAGGCGT

CGATGTCGTCGCCGTCCTCGCTGCTGCACTGGACCCGGCG

GATGATCGAGATCCGTAAGCAGAACCCGGCGTTCGGCCTC

GGCTCGTACACCGAACTCCAGTCCTCGAACCCGGCCGTCC

TCGCGTTCCTGGGGGAGGCCCCCTCGACCGGGGGGAACGG

GGACGACCTGGTGCTGTGCGTGCACAACTTCTCCCGGTTC

GCGCAGCCCACGGAGCTGGATCTGGGGGCGTTCAGCGGGG

GTCATGGGGTCGAGCTGATCGGCGGTGTCCGCTTCCCGGC

CATCGGGGAACTCCCGTATCTGCTGACCGTGGGAGGCCAC

GGCTTCTACTGGTTCGGGCTCCGCAAGGACGCCGTCTAG

[Sequence 23]
(SEQ ID NO: 23)
GTGTTCATGCAGGTCTGGCCTGGAGAGGGGTATCCACTGG

GTGCCACGTACGACGGCGCCGGCACCAACTTCGCGGTGTT

CACGGAGGCCGCCGACCGAGTAGAGCTGTGTCTGCTGCAC

GACGACGGTTCGGAGACGGCGGTCGAGCTGCGGGAGAGCG

ATGCCTTCGTGCGGCACGCGTACGTGCCGGGCGTGATGCC

-continued

GGGGCAGCGGTACGGCTACCGCGTGCACGGCCCGTACGCC

CCGGAGCGCGGACTGCGCTGCAACAGCGCCAAGCTGCTCC

TCGATCCGTACGCGCGTGCGATCAGCGGGGAGGTCCAGTG

GGGCGAGGAGGTGTACGGCTACCACTTCGGCGCACCCGAA

CGGCGCAACGACCTCGACTCGGCCCCGCACACGATGACGT

CGGTCGTGGTCAACCCGTACTTCGACTGGGGCGACGACCG

GCGCCCCGTACGGAGTACCACCACACGGTGATCTACGAG

GCCCACGTGAAGGGCCTGACCATGCGCCACCCGGGCCTGC

CCGAGGAGCTGCGGGGCACCTACGCGGCCCTCGCGCACCC

GGCGCTCATCGAGCACCTCACGGGGCTCGGGGTGACCGCG

CTGGAGCTGATGCCGGTCCATCAGTTCGTCAACGACCACC

GGCTGGTGGACATGGGCCTCAACAACTACTGGGGCTAGAA

CACGGTCGGGTTCTTCGCCCCGCACAACGCCTACGCCTCC

TGGGGCGACGGGGGCGAGGAGGTGCTGGAGTTCAAGTGGG

GGGTCAAGGCGCTGCACGAGGGGGGGATCGAGGTGATCCT

CGACGTGGTCTACAACCACACCGCGGAGGGCAACCACCTG

GGCCCGACGCTGTCCTTCAAGGGGCTGGACAACCCCTCGT

ACTACCGGCTGGCCGACGACCCCCGCTACTAGATGGAGAG

CACGGGGACCGGGAACTCGCTGCTCATGCGGTCCCCGCAC

GTACTCCAGATGATCATGGACTCACTGGGGTACTGGGTCA

CCGAGATGCACGTGGACGGGTTCCGTTTCGACCTCGCGGC

CACGCTGGCCCGGGAGTTCCACGAGGTGGACCGGCTGTCG

TCGTTCTTCGACCTGGTGCAGCAGGACCCCGTGGTCTCGC

AGGTGAAGCTGATCGCCGAGCCGTGGGACGTGGGCGAGGG

GGGCTACCAGGTGGGCAACTTCCCGCCGCTGTGGACCGAG

TGGAACGGCAAGTACCGGGACACGGTGCGGGACCTGTGGC

GCGGCGAGCCGCGACGCTGGCGGAGTTCGCGTCCCGGCT

GACCGGTTCCTCCGACCTCTACCAGGACGACGGGGGCCGC

CCGCTGGCCTCGATCAACTTCGTGACCTGCCACGACGGCT

TCACCCTGCACGACATGGTGGCCTACAACGACAAGCACAA

CCACGCCAACGGCGAGGACAACCGGGACGGCGAGAGCCAC

AACCGTTCCTGGAACTGCGGTGTCGAGGGCGACACCGACG

ATCCGGGGGTGCTGGAGCTGGGGCGCGGCAGATGCGCAA

CTTCATCGCCACGCTGCTGCTCTCCCAGGGCGTCCGGATG

CTCAGCCACGGCGACGAGTTCGCCCGCACCCAGCGGGGCA

ACAACAACGCCTACTGCCAGGACAACGAGCTGGCGTGGGT

GGCGTGGCCCGAGGACGGCCACGACCTCCTGGAGTTCACC

CGCGCGATGGTCTGGCTGCGCAAGGACCACCCGGTCCTGC

GCAGGGGCCGCTTCTTCCAGGGGGGCCCGGTGCAGGGCAC

CCACGACGAGCTGTCGGACATCGCCTGGTTCACGCCGGAG

GGGGGGGAGATGGCCCAGGGGGACTGGAACTCGGCACGGG

CCTCCGCGCTCACGGTCTTCCTGAACGGCAACGCGATCTC

CGAGCCCGGCACCCGGGGGGAACGCATCGCCGACGATTCG

TTCCTGCTGATGTTCAAGGGGGGGCGAGGGGGCTGGACT

TCGTGGTGCCGGTCGATCACGGCCGGCAGTGGGAGGTGGT

CGTCGACACCGCTCTGACGGGGGGGTGCCCAGGGGCACG

GGCCCGAAGGTGCAGGCCGGGGACCGGCTGACCCTCCTGG

ACCGGAGCCTGACGGTGTTGCAGCGGCCGGTGTAG

[Sequence 24]
(SEQ ID NO: 24)
ATGCAGGTCTGGCCTGGAGAGGCATATCCACTCGGCGCCA

CGTACGACGGGGGGGTACCAATTTCGCGGTCTTCTCGGA

GGCCGCCCATCGGATCGAGCTGTGTCTGCTGCACGACGAC

GGCTCGGAGAGGGGGTGGAACTGAGGGAGACCGACGCGT

TCGTGCGGCACGCGTATCTGCCCGGGGTCATGCCGGGGCA

GCGGTAGGGCTTCCGCGTGCACGGCCCGTTCGCGCCGGGG

GGCGGGGTGCGCTGCAATTCCGCCAAGCTGCTGCTCGATC

CGTACGCGAAGGCGATCAGCGGCGAGATCAAGTGGGGGGA

GGAGGTGTAGGGGTACCACTTCGGCGCCCCCGACAAGCGC

AACGACCTGGACTCGGCGCCGCACACGATGACCTCGGTCG

TGATCAACCCGTACTTCGACTGGGGCAACGACCGGCGGCC

GCGCACCGAGTACCACCACACAGTGCTCTAGGAGGCCCAT

GTGAAGGGCCTGACGATGGGGCATCCCGCGCTGCCCGAGG

AACTGGGGGCACGTATGCGGCGCTCGCCCACCCCGCCAT

CATCGAACACCTGACTGAACTGGGCGTCACCGCGCTCGAA

CTGATGGGGGTGCACCAGTTCGTGAACGACCACCGTCTGG

TGGACATGGGCCTGAACAACTACTGGGGCTACAACACGAT

CGGTTTCTTCGCCCCGCACAACGCGTACGCCTCCTGGGGC

GACCGCGGCCAGCAGGTGCTGGAGTTCAAGTCGGCAGTGA

AGGCGCTGCACGAGGCCGGGATCGAGGTCATCCTGGACGT

GGTCTACAACCACAGGGGGGAGGGCAACCACATGGGCCCG

ACGCTCTCCTTCAAGGGGATCGAGAACGCGTCGTACTACC

GGCTCACCGAGGATCCCCGCTACTACATGGACACCAGGGG

GACCGGGAACTCCCTCCTCATGCGCTCCCCGGACGTCCTC

CAACTGATGATGGACTGGCTGCGCTACTGGGTCAGCGACA

TGCATGTCGACGGCTTCCGCTTCGACCTCGCGGCCACCCT

GGGGGGGGAGTTCGACGAGGTGGACCGGCTGTCGTCGTTG

TTCGAGCTGGTCCAGCAGGACCCGGTGGTCTCCCAGGTGA

AGCTGATCGCCGAGCCGTGGGACGTCGGCGAGGGGGGCTA

CCAGGTGGGCAACTTCCCGCCGCTGTGGACCGAGTGGAAC

GGGAAGTACCGCGACAGGGTGGGGGACATGTGGGGGGCG

AGCCGCGTACGCTCGCGGAGTTCGCCTCCCGCCTGAGGGG

CTCGTCGGACCTCTACCAGGACGACGGCCGCCGTCCCCTC

GCCTCCATCAACTTCGTCACCTGCGACGACGGTTTCACCC

TGCACGACCTCGTCGCGTACAACGACAAGCACAACCAGGC

CAACGGCGAGGACAACCGGGAGGGGGAGAGCCACAACCGG

TCCTGGAACTGGGGGCCGAGGGCGACACCGAGGATCCGG

CGGTGCTGGCGTTGGGGCGCGCCAGATGCGCAACTTCAT

CGCCACGCTGATGCTCTCGCAGGGCGTGCCGATGCTCAGC

CACGGGGATGAGTTCGCGGGCACCCAGGGGGGCAACAACA

ACGCGTACTGCCAGGACGGCGAGCTGTCGTGGGTGGCGTG

GCCCGAGGACGGCAGCGAGCTGCTGGAGTTCACGCGCGCG

ATGGTGTGGCTGCGGCGCGACCATCCGGTCTTCCGGCGCC

GCCGCTTCTTCCACGGGGGGCCGGTGGAGGGCACGCACGA

CGAGCTGTCGGACATCGTCTGGTTCACGCCGACGGGTGAG

GAGATGATCCAGCGCGACTGGGATTCGGCGCAGGCACGGG

CGCTGACGGTGTTCCTCAACGGCACCGCGATCTCCGAGCC

CGGCCCACGCGGAGAGCGGATCTCGGACGACTCCTTCCTG

TTGATGTTCAACGCCTCCCCGAAGTCGCTGGAGTTCGTGG

TGCCGGTCGACCACGGCCGCCAGTGGCAGGTCGTCGTCGA

GACGGCACGCACGGACGGGATCCCGCCGGGCACGGTCGCG

AAGGTCAAGGCCGGGGACCGGCTGACGCTGGTGGACCGGA

GCCTCACGGTGTTGGAGGGGGGGCGTGA

In one embodiment, the bacterium of the present disclosure is a bacterium in which a function of transaldolase is deleted or attenuated. In another embodiment, the bacterium of the present disclosure is a bacterium in which a function of propionyl CoA carboxylase is deleted or attenuated. In yet another embodiment, the bacterium of the present disclosure is a bacterium in which a function of trehalose synthase is deleted or attenuated. In another embodiment, the bacterium of the present disclosure is a bacterium in which at least one or more of the above functions are deleted or attenuated, such as a bacterium in which the functions of transaldolase and propionyl CoA carboxylase are deleted or attenuated, a bacterium in which the functions transaldolase and trehalose synthase are deleted or attenuated, or a bacterium in which the functions transaldolase, propionyl CoA carboxylase and trehalose synthase are deleted or attenuated.

In one embodiment, a function of an enzyme may be controlled by a DNA sequence encoding the protein, may be controlled at a transcriptional stage of the protein, may be controlled at a translational stage of the protein, or may be controlled at a post-translational stage of the protein. Preferably, a function of an enzyme is controlled by the DNA sequence encoding the protein.

In one embodiment, a function of an enzyme may be controlled by a DNA sequence encoding the protein, for example, the function may be deleted or attenuated by a mutation in the DNA sequence encoding the protein.

In one embodiment, a function of an enzyme may be controlled at a transcriptional stage of the protein, for example, the function may be deleted or attenuated by modifying a function of a cis or trans element of the DNA sequence encoding the protein.

In one embodiment, a function of an enzyme may be controlled at a translational stage of the protein, for example, the function may be deleted or attenuated by a mutation of the Shine-Dalgarno sequence for translation of the protein.

In one embodiment, a function of an enzyme may be controlled at a post-translational stage of the protein, for example, the function may be deleted or attenuated by treating the protein with an inhibitor.

In the present disclosure, a mutation includes a substitution, an addition, a deletion or a recombination.

Those skilled in the art may, for example, confirm a mutation of a gene encoding a protein, confirm a transcription of the protein, or confirm an activity the protein or an amount of the protein according to known techniques, to confirm whether the enzyme function is deleted or attenuated.

A function of an enzyme may be deleted or attenuated under a condition where a bacterium is used for a production of sedoheptulose. A deletion of an enzyme function refers to a state in which the function of the enzyme of a bacterium used in the present invention cannot be confirmed by those skilled in the art based on known techniques. Attenuation of an enzyme function refers to a state in which the function of the enzyme of a bacterium used in the present invention is attenuated as compared with normal state. More specifically, for example, attenuation of an enzyme function is a state in which the function is 90%, 80%, 70%, 60%, 50%, 40%, 30%, 20%, 10%, 5%, 2.5% or less than 1% as compared to the function when culturing a wild type bacteria under a normal culture condition. For example, in the case of attenuation due to an introduction of a mutation, comparison may be made under the same culture condition as in the wild type, and in the case of attenuation due to an inhibitor, comparison may be made under the same conditions except for presence or absence of the inhibitor.

Examples of a bacterium in the present disclosure include, but not limited to, actinomycete, *Escherichia coli* and *Bacillus subtilis*, a bacterium belonging to *Flavobacterium*, and a bacterium belonging to *Achromobacter*. In a preferred embodiment, the bacterium is actinomycete, *Bacillus subtilis*, a bacterium belonging to *Flavobacterium*, or a bacterium belonging to *Achromobacter*. In a more preferred embodiment, the bacterium is actinomycete.

In the present disclosure, "actinomycete" refers to a Gram-positive bacterium belonging to the phylum actinomycete (Actinobacteria). "Actinomycete" includes, but not limited to, for example, *Streptomyces* genus such as *Streptomyces lividans, Streptomyces violaceoruber, Streptomyces coelicolor, Streptomyces avermitilis*, and *Streptomyces griseus; Actinosynnema* genus such as *Actinosynnema pretiosum*, and *Actinosynnema mirum; Pseudonocardia* genus such as *Pseudonocardia autotrophica, Pseudonocardia thermophila*; and *Corynebacterium* genus such as *Corynebacterium glutamicum*. In a preferred embodiment, the actinomycete is a bacterium belonging to *Streptomyces* or *Corynebacterium* genus, more preferably a bacterium belonging to *Streptomyces* genus, and even more preferably, the bacterium belonging to *Streptomyces* genus is *Streptomyces lividans* or *Streptomyces avermitilis*. The route for obtaining actinomycete is not particularly limited, and for example, it may be isolated from the soil, or may be obtained from a microorganism depository institution.

In the present disclosure, a bacterium used in a production of sedoheptulose is a bacterium that may biosynthesize sedoheptulose. For example, the bacterium used in a production of sedoheptulose is a bacterium having a sedoheptulose biosynthetic enzyme gene. The bacterium used for the production of sedoheptulose may be a wild type strain or a strain that have been artificially mutated. Examples of an artificial mutagenesis include a gene recombination, UV irradiation, X-ray irradiation, and a treatment with a mutagen. The bacterium used for the production of sedoheptulose may be a naturally occurring mutant strain. The bacterium used for the production of sedoheptulose also includes a bacterium having a homologous or heterologous sedoheptulose biosynthetic enzyme gene. For example, the bacterium used for the production of sedoheptulose may be a bacterium in which a heterologous sedoheptulose biosynthetic enzyme gene has been introduced by gene recombination. A method widely known in the art may be used to introduce the heterologous gene into the above-mentioned bacterium.

In the present disclosure, sedoheptulose may be produced intracellularly or extracellularly, preferably extracellularly. In the present disclosure, "bacterial cells" refers to bacterial cells. In addition, in the present disclosure, the "extracellular culture solution" refers to a portion of the culture solution obtained by culturing the bacterium and excluding the bacterial cells from the solution. That is, the extracellular culture solution comprises, for example, various components contained in the medium used for culture, and substances produced by a bacterium during culture.

In the present disclosure, a method for separating the bacterial cells and the extracellular culture solution is appropriately selected by those skilled in the art. For example, the culture solution obtained by culturing the bacterium may be subjected to centrifugation to separate the bacterial cells and the extracellular culture solution. As the centrifugation conditions such as temperature, time and speed, a well-known condition to a skilled person in the art may be used depending on the type of the bacterium used for culture. Alternatively, the bacterial cells and the extracellular culture solution may be separated by filtering the culture solution obtained by culturing the bacterium using an appropriate filtration membrane.

In the present disclosure, the separated extracellular culture solution itself may be used, or may be dried to be used as a composition containing sedoheptulose, or the produced sedoheptulose may be recovered from the extracellular culture solution. The term "recovery" means to obtain a solution mainly containing sedoheptulose, excluding various components and/or a bacterial cell contained in the medium used for culture. The proportion of sedoheptulose in the solution mainly containing sedoheptulose may be appropriately determined by those skilled in the art according to the purpose. A produced sedoheptulose may also be recovered as sedoheptulosan by acid treatment (Patent literature 5).

The produced sedoheptulose may be appropriately converted in or out of the cells to achieve a purpose by a technique known to those skilled in the art. Sedoheptulose may be converted chemically, enzymatically, or physicochemically, including phosphorylation, isomerization, cyclization, polymerization, acylation, galloylation, and dehydration cyclization. Converted sedoheptulose is for example sedoheptulose-7-phosphate, 7-O-galloyl-D-sedoheptulose and sedoheptulosan.

In one embodiment, a specific example of the production amount of sedoheptulose is, for example, preferably 3 g/L or more, more preferably 5 g/L or more in 7 days, or preferably 5 g/L or more, more preferably 10 g/L or more in 9 days. In still another specific example, the maximum sedoheptulose production amount during culture is preferably 5 g/L or more, more preferably 10 g/L or more, still more preferably 25 g/L or more.

According to the present disclosure, productivity of sedoheptulose by a bacterium may be improved. An improvement of productivity of sedoheptulose due to a deletion or attenuation of specific enzyme function means increase of productivity of sedoheptulose by the deletion or attenuation of specific enzyme function, or decrease of time until reaching specific productivity of sedoheptulose by the deletion or attenuation of specific enzyme function. More specifically, for example, 2 times or more, preferably 3 times or more, and more preferably 4 times or more of sedoheptulose is produced as compared with the case of culturing a wild type bacterium under normal culture conditions for 10 days of culture. In addition, when a wild type bacterium does not produce sedoheptulose under normal culture conditions, it may be allowed to produce sedoheptulose by a deletion or attenuation of the function of a specific enzyme.

In the production of sedoheptulose using a bacterium, those skilled in the art may appropriately change the culture conditions of the bacterium. A Culture condition of the bacterium may be changed by, for example, temperature, a carbon source, a nitrogen source, culture time, medium, oxygen content, pH, or an additive such as an antibiotic, for example, tetracycline (Non-patent literature 5).

In another embodiment, the present invention provides the above-described method of the present invention, further comprising the step of adding a carbon source to the medium. The further addition may be carried out at any time during culture of the bacterium, and it may be carried out continuously or intermittently. Desirably, the carbon source is further added so that the bacterium will not lyse. The lysis of a bacterium may be confirmed, for example, by measuring the pH of the culture solution. For actinomycete, desirably, the carbon source is further added so that the pH of the medium does not exceed 8.0. The lysis of a bacterium may also be confirmed by a decrease in the amount of the bacterium in the medium.

A Carbon source used in the present invention include, but not limited to, glucose, sucrose, fructose, mannitol, sorbitol, galactose, maltose, xylose, glycerol, ribose, gluconolactone or gluconic acid or salts thereof. In a preferred embodiment, the carbon source is glucose or glycerol. In another preferred embodiment, the carbon source does not contain ribose.

When the carbon source in the medium is consumed, various organic acids are produced as metabolites and the medium is acidified. The production of sedoheptulose by a bacterium is reduced due to acidification of the medium. Therefore, an alkalizing agent may be added to the medium so that the medium is not acidified. In case that actinomycete is used, an alkalizing agent is added to the medium so that the pH of the medium is not lowered below 5.0, preferably 5.5. The alkalizing agent includes, but not limited to, a carbonate such as calcium carbonate, magnesium carbonate, sodium carbonate, and sodium hydrogen carbonate, a hydroxide such as sodium hydroxide, potassium hydroxide, calcium hydroxide and magnesium hydroxide, ammonia, urea, and Calcium oxide. In a preferred embodiment, the alkalizing agent used in the present invention is a carbonate such as calcium carbonate, magnesium carbonate, sodium carbonate and sodium hydrogen carbonate. The alkalizing agent may be added to the medium before culture or may be added during culture. Further, the addition of the alkalizing agent may be continuous or intermittent addition. The amount of alkalizing agent to be added may be determined by measuring the pH of the medium, without difficulty. A pH may be measured by a known method, for example, using a pH meter.

Therefore, it may be effective for increasing the production of sedoheptulose to add a carbon source which is a raw material of sedoheptulose to the medium that may prevent a pH increase of the medium and to add an alkalizing agent to prevent a pH decrease of the medium.

In the present invention, the medium for culturing the bacterium and other culture conditions (for example temperature, time, pH, presence or absence of stirring) are appropriately selected by those skilled in the art according to the type of the bacterium to be cultured. Examples of more specific conditions include, but not limited to, pH 5 to 8, temperature 10 to 45° C., time 5 to 50 days.

The invention further provides the following aspects:
(1) a method for improving productivity of sedoheptulose, comprising culturing a bacterium in which a function of transaldolase is deleted or attenuated;
(2) the method according to (1), where the bacterium is a bacterium in which a function of propionyl CoA carboxylase and/or a function of trehalose synthase is/are further deleted or attenuated;
(3) the method according to (1) or (2), where the bacterium is actinomycete, *Bacillus subtilis*, a bacterium belonging to *Flavobacterium*, or a bacterium belonging to *Achromobacter*;
(4) the method according to (3), where the bacterium is actinomycete;
(5) the method according to (4), where the actinomycete is a bacterium belonging to *Streptomyces*; or
(6) the method according to (5), where the bacterium belonging to *Streptomyces* is *Streptomyces lividans* or *Streptomyces avermitilis*.

Hereinafter, the present invention will be described specifically and in detail with reference to Examples, but the Examples are used for illustrating the present invention and are not intended to limit the present invention.

EXAMPLE

Example 1

1. Production of Sedoheptulose Using *Streptomyces*

The inventor of the present application used *Streptomyces lividans* and *Streptomyces avermitilis* as a host to prepare a sedoheptulose producing strain, and examined the amount of sedoheptulose in the culture solution.

1-1. A Disruption of a Transaldolase Gene 1-1-1. A Disruption of a Transaldolase Gene in *Streptomyces lividans*

The transaldolase gene (SLI_2249) of *Streptomyces lividans* strain 1326 (NITE deposit number: NBRC 15675) was disrupted by homologous recombination. Transformation of *Streptomyces lividans* was performed according to a conventionally known method. Positions 1 to 1119 of SLI_2249 were disrupted and the gene disruption was confirmed using the primers AAGATCCCGGTCTTCGAGGCGGGCAAGGGC (SEQ ID NO. 25) and GCGGCGTAGGTGTCGGTCTTCGACTTGGGG (SEQ ID NO: 26).

1-1-2. A Disruption of a Trehalose Synthase Gene in *Streptomyces lividans*

The transaldolase gene (SLI_2249)-disrupted strain for *Streptomyces lividans* 1326 was used as a host, and the trehalose synthase gene (SLI_7555) was disrupted by homologous recombination. Transformation of *Streptomyces lividans* was performed according to a conventionally known method. Positions 1 to 1719 of SLI_7555 were disrupted and the gene disruption was confirmed using the primers CAAAGGCCGCAACAACACCCTCTCCGCC (SEQ ID NO: 27) and TAGCCCGCGCAGAACGCCTCCCGGCA (SEQ ID NO: 28).

1-1-3. A Disruption of a Propionyl CoA Carboxylase Gene in *Streptomyces lividans*

The transaldolase gene (SLI_2249)-disrupted strain for *Streptomyces lividans* 1326 was used as a host, and the propionyl CoA carboxylase gene (SLI_5198) was disrupted by homologous recombination. Transformation of *Streptomyces lividans* was performed according to a conventionally known method. Positions 1 to 1593 of SLI_5198 were disrupted, and the gene disruption was confirmed using the primers

```
                                       (SEQ ID NO: 29)
CCCAGGATGAGCCCCTCGAGGCGCAG
and (SEQ ID NO: 30)
CTGATCGTGCTGCTGCTGATGACGTACGA.
```

1-1-4. A Disruption of a Transaldolase Gene in *Streptomyces avermitilis*

The transaldolase gene (sav6314) of *Streptomyces avermitilis* strain MA-4680 (NITE deposit number: NBRC 14893) was disrupted by homologous recombination. Homologous recombination of *Streptomyces avermitilis* was performed according to a conventionally known method. The positions 1 to 1119 of sav6314 were disrupted, and the gene disruption was confirmed using the primers TCCGCCGACCTGGCCGGCTCGAACAACACC (SEQ ID NO: 31) and GCCAGCCGGCCGCGTACTGTCCGCGGACGG (SEQ ID NO: 32).

1-2. Preculture of *Streptomyces lividans* and *Streptomyces avermitilis*

A glycerol stock of spores of *Streptomyces: Streptomyces lividans* strain 1326, *Streptomyces lividans* strain 1326ΔSLI_2249, *Streptomyces lividans* strain 1326ΔSLI_2249ΔSLI_5198, *Streptomyces lividans* 1326ΔSLI_2249ΔSLI_7555 strain, *Streptomyces avermitilis* MA-4680 strain and *Streptomyces avermitilis* MA-4680Δsav6314 that were produced in 1-1 above was added to 5 mL of TSB medium (see Table 1 below). These actinomycetes were cultured at 28° C., 160 rpm for 72 hours with shaking.

1-3. Main Culture of *Streptomyces lividans* and *Streptomyces avermitilis*

A 0.1% volume of preculture solution was added to 50 mL of TSB medium (see Table 1 below) in a 500 mL baffled flask. Glucose was further added to the TSB medium at the start of culture so that the initial glucose concentration was 80 g/L.

During culture, the culture was shaken at 28° C., 160 rpm for 2 weeks while glucose was supplemented so that glucose was not exhausted.

TABLE 1

| TSB medium | |
|---|---|
| Pancreatic digest of casein | 17 g (1.7%) |
| Papaic digest of soybean | 3 g (0.3%) |
| Glucose | 2.5 g (0.25%) |
| NaCl | 5 g (0.5%) |
| $K_2HPO_4$ | 2.5 g (0.25%) |

1-4. Sedoheptulose Measurement

During the main culture, 1 mL of the culture solution was collected at a predetermined time and optical density at 600 nm was measured. The collected culture solution was centrifuged at 14000 rpm for 20 minutes to obtain a culture solution sample. The production amount of sedoheptulose in the culture solution sample was measured by HPLC. The HPLC measurement conditions are as shown in the table below.

TABLE 2

| Column: | Aminex HPX-87C |
| | (9 μm; 7.8 φmm × 300 mm) |
| | (Bio-Rad Laboratories, Inc.) |
| Solvent: | $H_2O$ |
| Detector: | RID |
| Standard sample: | Sedoheptulose (Sigma-Aldrich Co. LLC) |
| Flow rate: | 0.6 mL/min |
| Column temperature: | 85° C. |
| Retention time: | Sedoheptulose: around 12 min |

1-5. Result

Figure 2:
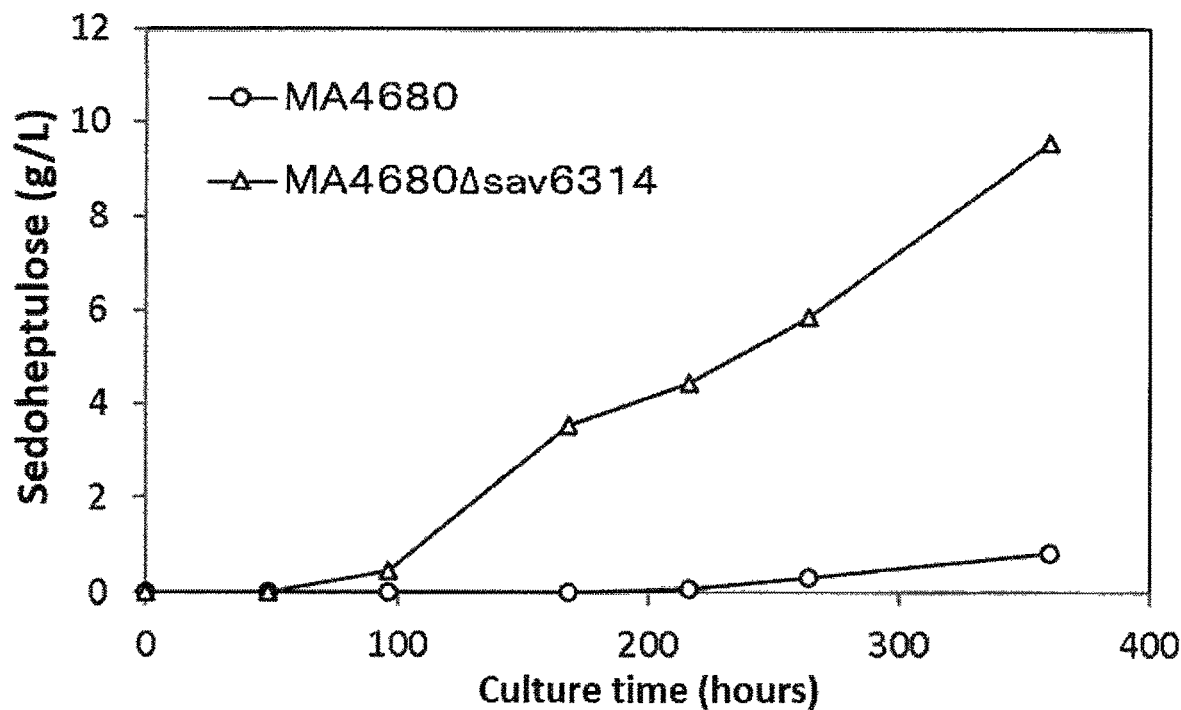
FIG. 2 shows the results of the production of sedoheptulose using *Streptomyces avermitilis* MA-4680 strain.
Figure 3:
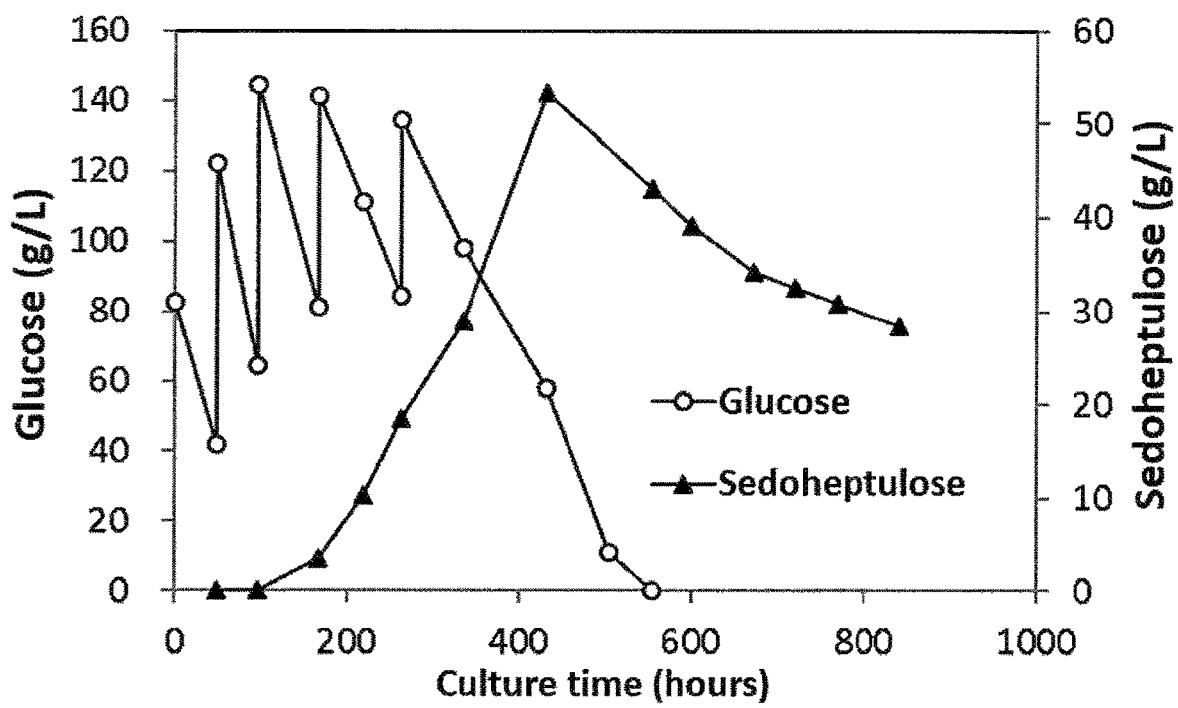
FIG. 3 shows changes in the productivity of sedoheptulose after culturing the *Streptomyces lividans* 1326ΔSLI_2249ΔSLI_5198 strain for a long period of time and stopping the supplemental addition of glucose.

The results for the *Streptomyces lividans* strain 1326 are shown in FIG. 1, and the results for the *Streptomyces avermitilis* strain MA-4680 are shown in FIG. 2. For the *Streptomyces lividans* strain 1326, a production of sedoheptulose could not be confirmed after 2 weeks of culture. The *Streptomyces lividans* strain 1326ΔSLI_2249 produced up to 5.7 g/L of sedoheptulose in about 9 days of culture. The *Streptomyces lividans* strain 1326ΔSLI_2249ΔSLI_5198 produced 28.8 g/L of sedoheptulose in about 2 weeks of culture. The *Streptomyces lividans* strain 1326ΔSLI_2249ΔSLI_7555 produced 13.0 g/L of sedoheptulose in about 11 days of culture. The *Streptomyces avermitilis* strain MA-4680 produced 0.9 g/L of sedoheptulose after 2 weeks of culture. The *Streptomyces avermitilis* strain MA-4680Δsav6314 produced 9.5 g/L sedoheptulose in 2 weeks of culture. In *Streptomyces lividans* and *Streptomyces avermitilis*, a disruption of the transaldolase gene significantly increased productivity of sedoheptulose. Furthermore, a combination of a disruption of the trehalose synthase gene or the propionyl CoA carboxylase gene with a disruption of the transaldolase gene disruption, productivity of sedoheptulose was significantly improved. FIG. 3 shows changes in productivity of sedoheptulose after the *Streptomyces lividans* strain 1326ΔSLI_2249ΔSLI_5198 was cultured for a long period of time and the supplemental addition of glucose was stopped. Although the production of sedoheptulose was increased over time and sedoheptulose was produced at a maximum of 53.3 g/L in 431 hours during the supplemental addition of glucose, when the supplementation of glucose was stopped and glucose became depleted, it is observed that the productivity of sedoheptulose was decreased.

INDUSTRIAL AVAILABILITY

According to the present invention, there is to provide a method for producing sedoheptulose with a bacterium, a method for improving productivity of sedoheptulose with the bacterium, and the bacterium.

The invention claimed is:

1. A bacterium belonging to *Streptomyces*, in which a function of transaldolase is deleted or attenuated.

2. The bacterium of claim 1, wherein the bacterium is *Streptomyces lividans* or *Streptomyces avermitilis*.

* * * * *